(12) United States Patent
Clarke et al.

(10) Patent No.: US 9,125,397 B2
(45) Date of Patent: Sep. 8, 2015

(54) APPARATUSES AND COMPOSITIONS FOR CRYOPRESERVATION OF CELLULAR MONOLAYERS

(75) Inventors: Dominic M. Clarke, Bothell, WA (US); Ian B. Nicoud, Seattle, WA (US); Aby J. Mathew, Bothell, WA (US); Michael Rice, Woodinville, WA (US)

(73) Assignee: BioLife Solutions, Inc., Bothell, WA (US)

( * ) Notice: Subject to any disclaimer, the term of this patent is extended or adjusted under 35 U.S.C. 154(b) by 406 days.

(21) Appl. No.: 13/265,959

(22) PCT Filed: Apr. 29, 2010

(86) PCT No.: PCT/US2010/033032
§ 371 (c)(1),
(2), (4) Date: Oct. 24, 2011

(87) PCT Pub. No.: WO2010/127158
PCT Pub. Date: Nov. 4, 2010

(65) Prior Publication Data
US 2012/0040450 A1 Feb. 16, 2012

Related U.S. Application Data

(60) Provisional application No. 61/173,888, filed on Apr. 29, 2009.

(51) Int. Cl.
*A01N 1/00* (2006.01)
*C12M 3/00* (2006.01)
*A01N 1/02* (2006.01)

(52) U.S. Cl.
CPC .................................... *A01N 1/0242* (2013.01)

(58) Field of Classification Search
CPC ....... A01N 1/02; A01N 1/021; A01N 1/0242; A01N 1/0257; A01N 1/0263; C12M 23/12; C12M 23/42; C12M 41/12
See application file for complete search history.

(56) References Cited

U.S. PATENT DOCUMENTS 6,337,205 B1 * 1/2002 Wisniewski ............... 435/307.1
6,347,525 B2 2/2002 Cosman
(Continued)

FOREIGN PATENT DOCUMENTS

EP 0246824 B1 11/1987
WO 97/28402 A1 8/1997

OTHER PUBLICATIONS

Farrant, "Water Transport and Cell Survival in Cryobiological Procedures," Philos. Trans. R. Soc. London B278; 191-205; (1977).
(Continued)

*Primary Examiner* — Nathan Bowers
(74) *Attorney, Agent, or Firm* — K&L Gates LLP

(57) ABSTRACT

Provided are apparatuses for cryopreserving cells which include a vessel comprising a biocompatible substrate, wherein the vessel further comprises an interior and an exterior, and a mechanical ice nucleating device disposed in or on the vessel interior for initiating ice crystal formation. Also provided are kits comprising one or more apparatuses for cryopreserving cells and a biopreservation medium. Further provided are compositions comprising a vessel for holding cells, a mechanical ice nucleating device, a biopreservation medium, and cells disposed in the vessel. The apparatuses, kits, and compositions of the invention can optionally include an insulating material which is disposed on all or a portion of the vessel.

17 Claims, 24 Drawing Sheets

(56) References Cited

U.S. PATENT DOCUMENTS

| | | | |
|---|---|---|---|
| 6,361,934 B1 | 3/2002 | Acton et al. | |
| 6,453,683 B1 * | 9/2002 | Wisniewski et al. | 62/75 |
| 6,472,206 B1 | 10/2002 | Scholl et al. | |
| 6,492,103 B1 | 12/2002 | Taylor | |
| 6,599,696 B2 * | 7/2003 | Olson et al. | 435/4 |
| 6,994,954 B2 | 2/2006 | Taylor | |
| 7,341,829 B2 | 3/2008 | Scholl et al. | |
| 7,854,896 B2 * | 12/2010 | Tyndorf et al. | 422/547 |
| 2006/0053652 A1 | 3/2006 | Gyory et al. | |
| 2007/0186567 A1 | 8/2007 | Gasteyer et al. | |
| 2007/0254356 A1 * | 11/2007 | Wilson et al. | 435/297.5 |
| 2008/0003561 A1 | 1/2008 | Woods et al. | |
| 2008/0057040 A1 | 3/2008 | Crook et al. | |
| 2008/0114348 A1 | 5/2008 | Vancelette et al. | |
| 2008/0166753 A1 * | 7/2008 | Storey et al. | 435/32 |

OTHER PUBLICATIONS

Huang et al., "Cryopreserved Cell Monolayers for Rapid Detection of Herpes Simplex Virus and Influenza Virus," Journal of Clinical Microbiology, 40(11):4301-4303, (Nov. 2002).

Mazur, "Kinetics of Water Loss from Cells at Subzero Temperatures and the Likelihood of Intracellular Freezing," J Gen. Physiol., vol. 47, pp. 347-369, (Apr. 1963).

Mazur, "Freezing of Living Cells: Mechanisms and Implications," Am. J. Physiol. 247; Cell Physol. 16; C125-C142; (1984).

Mazur, "The Role of Intracellular Freezing in the Death of Cells Cooled at Supraoptimal Rates," Cryobiology, 14:251-272 (1977).

Mazur, Principles of Cryobiology, Life in the Frozen State, CRC Press, Boca Raton; pp. 3-65; (2004).

Morris, "Cryopreservation of Animal and Human Cell Lines," Methods Mol. Biol. vol. 368:179-187227-236; (1995).

Pasch et al., "Cryopreservation of Keratinocytes in a Monolayer," Cryobiology, 39:158-168; (1999).

PCT Written Opinion of the International Searching Authority for International Application No. PCT/US2010/033032, completed Jun. 16, 2010, 12 pgs.

\* cited by examiner

APPARATUSES AND COMPOSITIONS FOR CRYOPRESERVATION OF CELLULAR MONOLAYERS

REFERENCE TO RELATED APPLICATIONS

This application is a national phase application under 35 U.S.C. 371 of International Application No. PCT/US2010/033032, filed on Apr. 29, 2010, which claims priority to and the benefit of U.S. Provisional Application No. 61/173,888, filed Apr. 29, 2009, the entire disclosures of each of which are incorporated herein by reference.

BACKGROUND OF THE INVENTION

Cryopreservation is a process by which samples such as biological materials are frozen under controlled conditions and stored at low temperatures. Cryopreservation is frequently used to store cell cultures, for example, which must be maintained over time in order to ensure a ready supply of cells for re-growth and experimentation. Cells for such purposes are routinely frozen in suspension in industrial cryovials. Freezing methods have been developed to minimize the impact of osmotic shock and intracellular ice crystal formation, two factors that contribute to cell death during the freezing process and frozen storage.

Under current methods, however, a significant number of cells are still lost to cell death during the freeze-thaw process. Cell loss can be substantial in homogeneous cell suspensions, and cell loss increases as the system undergoing preservation becomes more complex (e.g., tissues and organs). Moreover, current methods are insufficient for effective large-scale cryopreservation of cell samples and tissues in a multi-vessel format, for example as adherent cells in a multiwell format. Unacceptably high well-to-well variability as well as unsatisfactory overall post-thaw viability currently render large-scale processes for bulk freezing of cells in multi-well plates commercially non-viable.

SUMMARY OF THE INVENTION

The present invention is based on the discovery that specially configured vessels, when combined with an optimized preservation media, can significantly reduce the well-to-well variability, and improve the integrity, viability, recovery and shelf-life of cryopreserved cells, including confluent cell monolayers. As described and contemplated herein, this discovery enables for the first time, a consistently available supply of reliable cryopreserved cells for a wide variety of relevant applications such as but not limited to disease diagnosis, toxicity screening and small molecule/pharmaceutical analysis. Set forth herein are exemplary embodiments which illustrate how to make, use and test the invention as well as teachings relating to the same which describe the present invention in a manner understood by the skilled artisan and which fully enable practice of the present invention by the skilled artisan.

The present invention relates to apparatuses, kits, and compositions for the freezing and cryopreservation of cultured cells and tissues. In one aspect, the invention provides apparatuses for the large-scale cryopreservation of cell cultures in biocompatible vessels, such as multiwell tissue culture plates, and an ice nucleating device which facilitates consistent well to well ice nucleation, a step necessary for the uniform survival of cells during the cryopreservation process.

The ice nucleating device is a mechanical (i.e., non-chemical) device which provides an initiation point for ice nucleation. The mechanical ice nucleating device can be located, for example, on the vessel cover, on the vessel itself, or on a vessel insert, such that the mechanical ice nucleating device becomes submerged in, or comes into contact with, the cryopreservation medium containing the biologic sample.

In some embodiments, the apparatuses of the invention can include an insulating material to facilitate effective cooling and warming. The insulating material is a mechanical component, which provides a means of thermal insulation to the exterior (e.g., periphery) or interior of the vessel. The insulating device can be located, for example, on the exterior space of a vessel such that the cooling and warming rates of the insulated portion of the vessel are similar to the other sections of the vessel. The insulating material can be disposed on the vessel, integral with the vessel, or detachable from the vessel. In some embodiments, the insulating material is located adjacent to, but not in contact with, the vessel.

The apparatuses of the invention can be used with a nutrient-rich biopreservation medium that is configured to optimally maintain cellular osmotic and ionic balances, control free radical accumulation, and reduce the stress responses under non-normothermic conditions. The preferred biopreservation medium for optimal storage and post-thaw recovery is CRYOSTOR™ (BioLife Solutions, Inc., Bothell, Wash.), but the apparatuses can be used with any suitable biopreservation medium.

In some embodiments, the combination of the insulating material, mechanical ice nucleating device and biopreservation (e.g., a freezing) medium allows for uniform ice nucleation and thawing, and improved post-thaw viability. Thus, the invention enables cells and tissues to be cryopreserved in ready-to-use configurations for high throughput analysis for screening or diagnostic purposes. Moreover, the present invention enables cell cultures to be frozen and stored for extended lengths of time via an easy-to-use method. The invention is particularly useful for the cryopreservation of fully intact, viable cell monolayers in ready-to-use formats for high throughput screening.

In another aspect, the invention provides an apparatus for cryopreserving cells. The apparatus includes a vessel comprising a biocompatible substrate. The vessel has an interior and an exterior. The apparatus can include a mechanical ice nucleating device which is disposed in or on the vessel interior and initiates ice crystal formation. In one preferred embodiment, the apparatus is sterile. In some embodiments, the exterior of the vessel includes an insulating material which contacts at least a portion of the vessel's exterior. In other embodiments, the insulating material can be included on or within the vessel.

In another preferred embodiment, the vessel is a multiwell cell or tissue culture plate (e.g., 6-well, 12-well, 96 well, 384-well, 1536-well). It will be appreciated that any multiwell formats can be used with the present invention.

In a preferred embodiment, the mechanical ice nucleating device includes one or more structural elements (e.g., a three dimensional protrusion) which occupy a portion of the vessel interior, such as but not limited to a protrusion which projects from a surface of the vessel interior, from a surface of a vessel cover, or from a surface of a vessel insert. In some embodiments, the mechanical ice nucleating device includes at least one physical anomaly on the interior surface of the vessel, such as but not limited to a score, a scratch, an etching, a nick, or other physical irregularity on a surface of the substrate. In some embodiments, the mechanical ice nucleating device is a plastic protrusion, or another three dimensional element.

The mechanical ice nucleating device can be integral with the vessel. The protrusion can be of any suitable shape (e.g., spike-like, needle-like, sphere-like, pyramid-like, or cone-like) or construction (e.g., hollow, solid, semi-permeable). In some embodiments, the mechanical ice nucleating agent is a removeable mesh or mesh-like insert. The mechanical ice nucleating device can also be or include a non-smooth coating on a surface of the vessel interior. In further embodiments, the vessel includes a separable cover, and the cover can include an ice nucleating device having a structural element which protrudes from a surface of the cover into the vessel interior. The ice nucleating device can be detachably connected to the cover, to the vessel, to a vessel insert. Alternatively, the ice nucleating device can be integral with the cover, the vessel, or the insert. In further embodiments, the ice nucleating device can be present on a vessel (e.g, a well) insert which vessel insert can be separable from the vessel.

In one embodiment, the apparatus can include a cryopreservation medium, CRYOSTOR™, or a functional equivalent.

In another aspect, the invention provides for an apparatus for cryopreserving a cell monolayer. The apparatus comprises a vessel, preferably a multiwell plate (e.g., a cell culture or tissue culture plate), and a mechanical ice nucleating device associated with at least one well of the multiwell tissue culture plate. The mechanical ice nucleating device can be integral with at least one well, or detachably associated with at least one well of the multiwell tissue culture plate. In some embodiments, the apparatus includes an insulating material which contacts at least a portion of the vessel. In some embodiments, the vessel is sterile.

In another aspect, the invention provides a vessel where an insulating material is disposed on all or a portion of the vessel's exterior to aid in cooling and warming of the vessel. In some embodiments, the insulating material can be disposed on the exterior or the vessel, the interior of the vessel, or both the exterior and interior of the vessel. The insulating material can be any type of material but in the preferred form the insulation would be the same material as that used to make the vessel and will aid in minimizing the variations in the cooling and warming rates from well to well in a multiwell vessel. Types of insulation are well known in the art and include but are not limited to caulks, foams, sprays, or strips of thermally insolative materials. In the preferred embodiment, the vessel is a multiwell plate and the insulating material is applied in the space between the exterior wells (i.e., the wells on the perimeter of the plate) and the outside edge of the plate. It is understood that any or all of the wells in a multiwell plate can be insulated with an insulation device as described herein. In some embodiments, the insulating material will be part of the interior of the vessel, for example, occupying some portion of a well or wells. In some embodiments, the insulation device can be an integral part of the vessel or the insulation device can be detachable.

In a further aspect, the invention provides an apparatus which includes a sterile vessel for holding cells or tissue, and a mechanical ice nucleating device disposed in said vessel. The apparatus can optionally include an insulating material disposed on all or a portion of the vessel.

In yet another aspect, the invention provides kits for cryopreserving cells. The kits can include any apparatus described herein and a biopreservation medium, such as the CRYOSTOR™ cryopreservation medium, or a functional equivalent.

In another aspect, the invention provides compositions. The compositions include a sterile vessel for holding cells. The vessel has an interior and an exterior. The composition also includes a mechanical ice nucleating device, a biopreservation medium (e.g., a cryopreservation medium or hypothermic preservation medium), and cells disposed in or in contact with the biopreservation medium within the interior of the vessel. The ice nucleating device can be a mechanical ice nucleating device, such as those mentioned above, which is disposed on or in the vessel interior. In some embodiments, the vessel is insulated with an insulating material. This and other aspects and embodiments of the present invention are suitable for the preservation of cells, whether progenitor, primary, immortalized, or other, as well as tissues.

In another aspect, the invention provides an apparatus for cryopreserving cells. The apparatus can include a vessel comprising a biocompatible substrate, wherein the vessel further comprises an interior and an exterior; an insulating material that is added to the free space surrounding the exterior or interior wells and/or occupying the interior space of at least one well of a multiwell vessel to aid in consistent cooling and warming of all wells; and a mechanical ice nucleating device disposed in or on the vessel interior for initiating ice crystal formation. In some embodiments, the apparatus is sterile. In some embodiments, the insulating material is comprised of the same material as the vessel, and in some embodiments the insulating material is comprised of a different material as the vessel. The insulating material can be, for example, any caulk, foam, spray, or sheet, which will provide an insulating effect. In some embodiments, the insulating material occupies a portion of the vessel exterior or any free space surrounding any well of a multi-well tissue culture plate. The insulating material optionally can occupy any or all of the vessels, so as to fill the air space above the top level of the cells and cryoprotectant media and the lower or bottom surface of the lid or cover. In some embodiments, the insulating material occupies both the exterior and interior spaces of the vessel. The insulating material can be attached to the vessel or vessel lid directly, and the insulating material can be detachable from the vessel or vessel lid.

In another aspect, the invention provides an apparatus for cryopreserving a cell monolayer. The apparatus can include a multiwell cell culture plate having a plurality of wells and, the multiwell cell culture plate forming at least one free space which not occupied by a well; an insulating material integral with or disposed in at least a portion of the at least one free space surrounding at least one well; and an ice nucleating device integral with at least one well of the multiwell cell culture plate.

In another aspect, the invention provides an apparatus for cryopreserving a cell monolayer. The apparatus can include a multiwell cell culture plate forming a plurality of wells, wherein each well has an interior space for containing fluid; a removable lid for covering the multiwell cell culture plate; an insulating material detachably associated with the lid, wherein the insulating material is configured to occupy the interior space of at least one well above the fluid; and an ice nucleating device integral with at least one well of the multiwell cell culture plate.

In another aspect, the invention provides an apparatus for cryopreserving a cell monolayer. The apparatus can include a multiwell cell culture plate; an insulating material integral with the exterior area of the vessel, or interior or exterior space surrounding at least one well; and an ice nucleating device detachably associated with at least one well of the multiwell cell culture plate.

In another aspect, the invention provides an apparatus for cryopreserving a cell. The apparatus can include a sterile vessel for holding cells or tissue, the vessel having an exterior surface; an insulating material integral with the exterior of the vessel; and a mechanical ice nucleating device disposed in said vessel. In some embodiments, the cells are in suspension.

In another aspect, the invention provides a composition. The composition can include a sterile vessel for holding cells, wherein the vessel further comprises an interior and an exterior; an insulating material; an ice nucleating device; a biopreservation medium; and cells disposed in or in contact with the biopreservation medium within the interior of the vessel. In some embodiments, the ice nucleating device comprises a mechanical ice nucleating device disposed on or in the vessel interior for initiating ice crystal formation. In some embodiments, the cells comprise primary cells, immortalized cells, or tissue. In some embodiments, the cells are monolayers or cells in suspension.

This Summary is provided merely to introduce certain concepts and not to identify any key or essential features of the claimed subject matter.

BRIEF DESCRIPTION OF THE DRAWINGS

The aspects, embodiments, and features of the invention can be better understood with reference to the drawings described below. The drawings are not necessarily to scale, emphasis instead generally being placed upon illustrating the principles of the invention. The drawings are provided to highlight specific embodiments of the invention and are not intended to limit the invention, the scope of which is limited only by the claims. In the drawings, like numerals are used to indicate like parts throughout the various views.

FIGS. 10A-C—were used), and with and without an insulating device in accordance with an illustrative embodiment of the invention.

DETAILED DESCRIPTION OF THE INVENTION

Figure 1A:
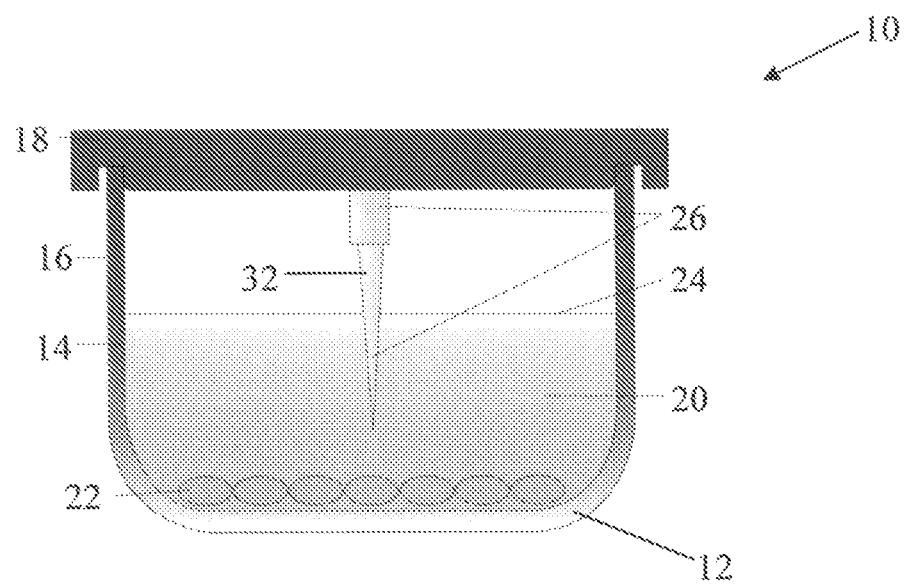
FIGS. 1A-D show cross-sectional views of ice nucleating devices, in accordance with an illustrative embodiment of the invention.

These and other aspects, embodiments, and features of the invention are also described in the following sections of the application, which are provided to highlight specific embodiments of the invention and are not intended to limit the invention, the scope of which is limited only by the claims.

The present invention provides apparatuses, kits and compositions for the freezing, thawing and use of cultured cells (e.g., cell monolayers, suspended cells) in multiwell vessel formats. In addition, the present invention is suitable for the preservation of cells, whether progenitor, primary, immortalized, or other, as well as tissues. In particular, the present invention overcomes the limitations met by previous inventions and meets the needs of providing a method, composition, and apparatus to produce uniformly frozen adherent cell monolayers in multiwell tissue culture plates that upon thawing yields acceptably uniform cell viability and functional performance levels in each of the wells of a tissue culture plate. Importantly, these criteria are uniform for each well of a multiwell plate following preservation allowing for accurate and immediate testing of the entire plate. The well-to-well uniformity and improved viability and function of cell culture monolayers allows, for example, pharmaceutical companies and toxicology testing laboratories to utilize the plated cells for high throughput screening of absorption, distribution, metabolism, excretion, and toxicology (ADME/T) of drug compounds in an in vitro model. Without the present invention, uniform cell density, viability, and functional performance among each of the wells could not be accomplished following cryopreservation and therefore this concept could not be practiced. The present invention will significantly reduce time and labor costs associated with high throughput screening of plated cells.

For the present invention, cell cultures are plated, for example, on multiwell tissue culture plates under standard culture conditions to obtain an adherent cell monolayer. Once the desired cell density level is attained, the cell culture medium is removed and replaced with chilled (preferably between 2 and 8° C.) CRYOSTOR™ cryopreservation medium containing 5 or 10% DMSO (BioLife Solutions, Inc., Bothell, Wash.). While CRYOSTOR™ is the most optimal and preferred cryopreservation media, alternative formulations could be used. Furthermore, the present invention is not limited to CRYOSTOR™ with 5 or 10% DMSO as other CRYOSTOR™ formulations with varying levels of DMSO can be applied. The current invention is also not limited to the use of DMSO as the cryoprotectant. The volume of the cryopreservation medium added should be at least enough to entirely cover the bottom of the desired well.

Designed to prepare and preserve cells in ultra low temperature environments (for example, about −80° C. to −196° C.), CRYOSTOR™ provides a non-toxic, protective environment for cells and tissues during the freezing, storage, and thawing process. CRYOSTOR™, a member of BioLife's HYPOTHERMOSOL® platform, is uniquely formulated to address the molecular-biological aspects of cells during the cryopreservation process thereby directly reducing the level of cryopreservation-induced cell death and improving post-thaw cell viability and function. Through modulating the cellular biochemical response to the cryopreservation process, CRYOSTOR™ provides for enhanced cell viability and functionality while eliminating the need to include serum, proteins or high levels of cytotoxic agents. CRYOSTOR™ has been shown to significantly improve cell viability and function following cryopreservation in comparison to traditional culture media+serum+DMSO approaches. In addition to improving overall cell survival and function, CRYOSTOR™ also provides the advantage of being a completely defined serum- and protein-free cryopreservation medium.

In one embodiment, the cryopreservation medium comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions, and combinations thereof. The cryopreservation medium additionally comprises a cryoprotectant. In some embodiments, the cryoprotectant is DMSO, and the DMSO is present at between about 0% to about 20%, such as, for example, 1%, 2%, 3%, 4%, 5%, 7%, 10%, 15%, or 20%. The cryopreservation medium can optionally comprise glutathione, a vitamin E derivative, an antioxidant, a caspase inhibitor, or combinations thereof.

It is understood that, when referenced throughout, CRYOSTOR™ is identified and referenced as an exemplary cryopreservation solution, respectively, and that the present invention contemplates CRYOSTOR™ as preferred embodiments of cryopreservation solutions, respectively, suitable for use with the tissues, cells, materials and methods set forth herein. It is further understood that the present invention also contemplates functional equivalents of CRYOSTOR™; all that is required is that a cryopreservation solution meet the functional requirements set forth herein and perform in a comparable manner when used in accordance with the present teachings.

Figure 1B:
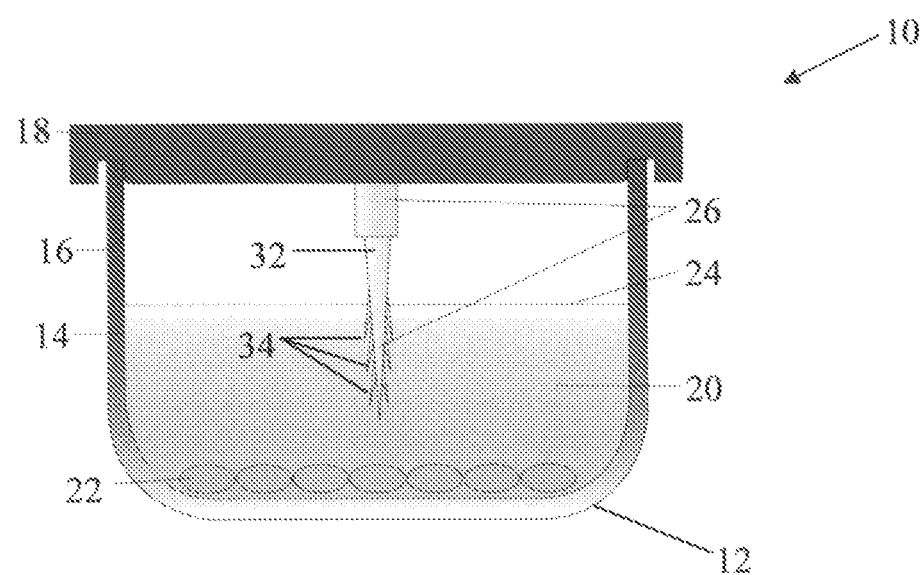

In one embodiment, the mechanical ice nucleating device is a needle-like protrusion that extends into the liquid medium of each well to be nucleated. The ice nucleating device can be attached to or integral with a vessel lid as shown in FIGS. 1A and 1B or a removable vessel insert as shown in FIGS. 1C-G and FIG. 10 A-C. In another embodiment, the ice nucleating device can be a part of the inner wall of the vessel. In yet another embodiment, the ice nucleating device can be placed directly in the fluid or in the well. One of skill in the art will appreciate that multiple and alternative ice nucleating devices can be used in a single vessel.

The apparatus can be sterile, and in preferred embodiments the apparatus is sterilized. The vessel (e.g., a well) can be made of plastic such as the plastic that comprises a multiwell tissue culture plate. The vessel can provide a substrate for the attachment and growth of cell cultures. In preferred embodiments, the growth and attachment of the cell cultures is in the form of a cellular monolayer. The fluid added to the vessel can be any fluid for the purpose of propagating, maintaining, or preserving the cell culture or cellular monolayer. In various embodiments, the fluid is CRYOSTOR™ a cryogenic compatible, serum-free, protein-free nutrient matrix solution.

In some embodiments, the ice nucleating device is a physically pointed projection having a rough (i.e., non-smooth surface). The ice nucleation device can be composed of any suitable material that promotes ice nucleation. In preferred embodiments, the ice nucleation device is made of the same material that the vessel (e.g., multiwell plate) is made of.

Referring to FIGS. 1A-D, cross-sectional schematic views of an apparatus 10 are shown, in accordance with an illustrative embodiment of the invention. The apparatus 10 includes a vessel 12 having an inner wall 14 and an outer wall 16. The vessel 12 can be, for example, a multiwell tissue culture plate having a plurality of wells. The apparatus 10 can include a removable lid 18 which covers the vessel 12. Vessel 12 is intended to contain a fluid overlay 20, such as cryopreservation media or growth media, that covers a cellular monolayer 22. The apparatus 10 further includes an ice nucleating device 26 which can be attached to or integral with the vessel lid 18, as shown in FIGS. 1A and 1B. The ice nucleating device 26 or the lid 18 are configured such that all or a portion of the ice nucleating device 26 comes into contact with the fluid overlay 20 in the vessel 12 when the lid 18 is placed on the vessel 12.

Figure 1C:
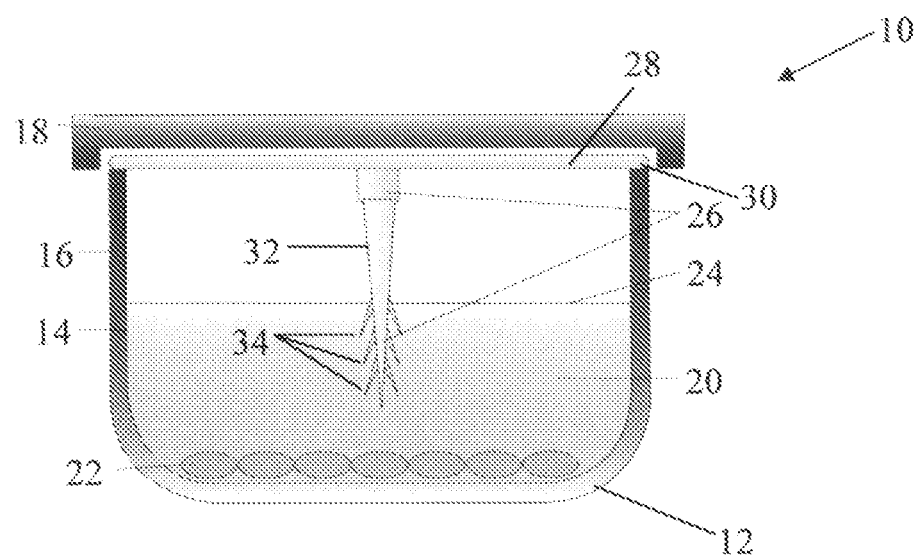
Figure 1D:
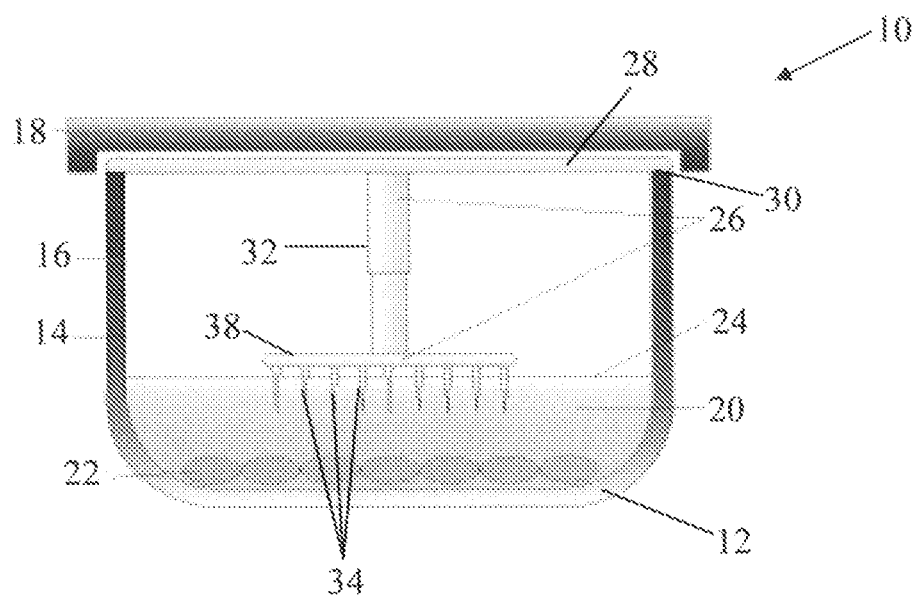

Referring to FIGS. 1C and 1D, in some embodiments the ice nucleating device 26 is attached to or integral with a removable insert 28 which is separable from the vessel 12 and the lid 18. The insert 28 can be configured to releasably engage the top 30 of the vessel 12 and/or can be configured to engage the inner wall 14 or outer wall 16 of the vessel 12. Vessel inserts are well known and a person of skill in the art will appreciate that many different insert configurations can be used in accordance with the invention. The ice nucleating device 26 or the insert 28 are configured such that all or a portion of the ice nucleating device 26 comes into contact with the fluid overlay 20 in the vessel 12 when the insert is placed in or on the vessel.

Referring to FIG. 1A, the ice nucleating device 26 can comprise a primary needle-like or spike-shaped protrusion 32. Referring to FIGS. 1B and 1C, the ice nucleating device 26 can include one or more secondary protrusions 34 that project from the primary protrusion 32. The secondary protrusions 34 provide additional nucleation sites for ice crystal formation.

Referring to FIG. 1D, the ice nucleating device 26 can comprise a stem 36 that supports a surface 38 which has one or more secondary protrusions 34. In some embodiments, only secondary protrusions 34 come into contact with the fluid overlay 20 in the vessel 12. The surface 38 can be any suitable shape and can be, for example, substantially disc-shaped and sized smaller than the vessel opening to provide many ice nucleation points across the entire vessel (e.g., a well).

In some embodiments, the ice nucleation device described herein is attached to or integral with an interior surface of the vessel, such as an inner wall or bottom.

In various embodiments, more than one ice nucleation device is disposed in or on the vessel.

Regardless of whether the ice nucleating device is located on the lid, on a removable insert, or on an interior surface of the vessel sidewall, the apparatus is configured such that one or more primary or secondary protrusions come into contact with the fluid overlay covering the cellular monolayer. In preferred embodiments, the protrusions of the ice nucleation device do not come in contact with the cell monolayer.

The invention is particularly useful for high throughput screening of multiwell plates. Thus, in preferred embodiments, the apparatus includes a tissue culture plate which comprises more than one vessel (i.e., well), such as 4-well, 6-well, 8-well, 12-well, 96-well, 384-well, or 1536-well plates. A person of skill in the art will appreciate that the invention can be used in connection with a multiwell plate having any number of wells.

Figure 1E:
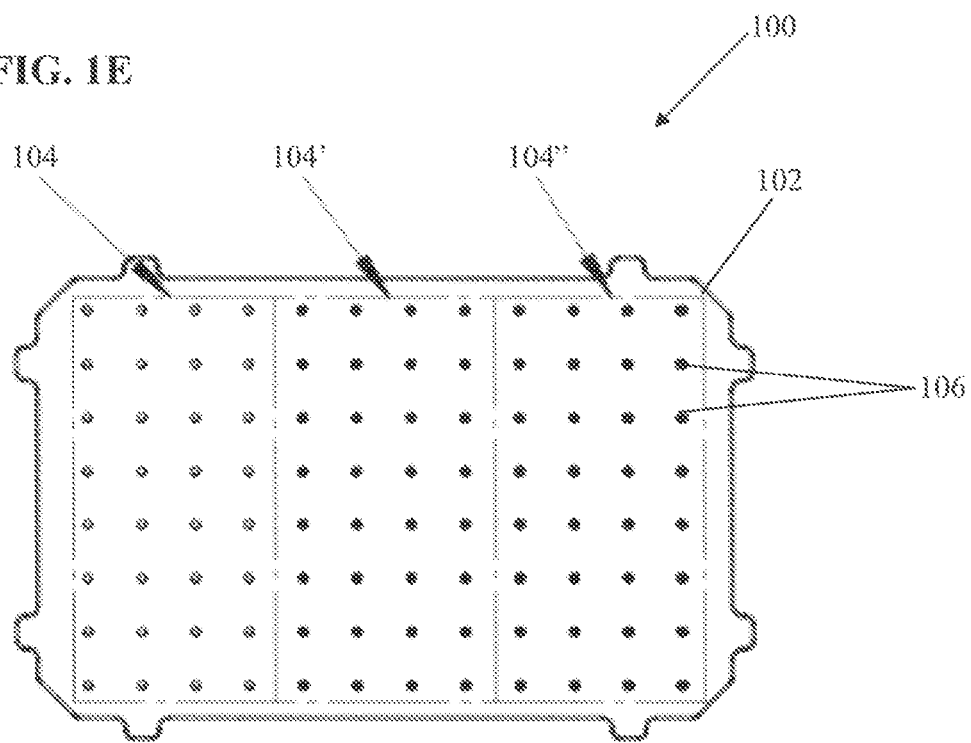
FIGS. 1E-G show a multiwell plate insert having a plurality of ice nucleating devices, in accordance with an illustrative embodiment of the invention.
Figure 1F:
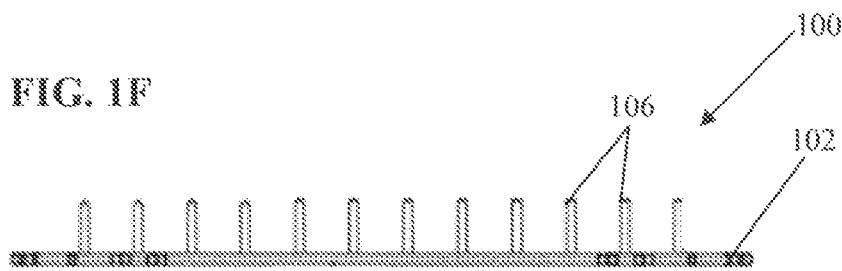
Figure 1G:
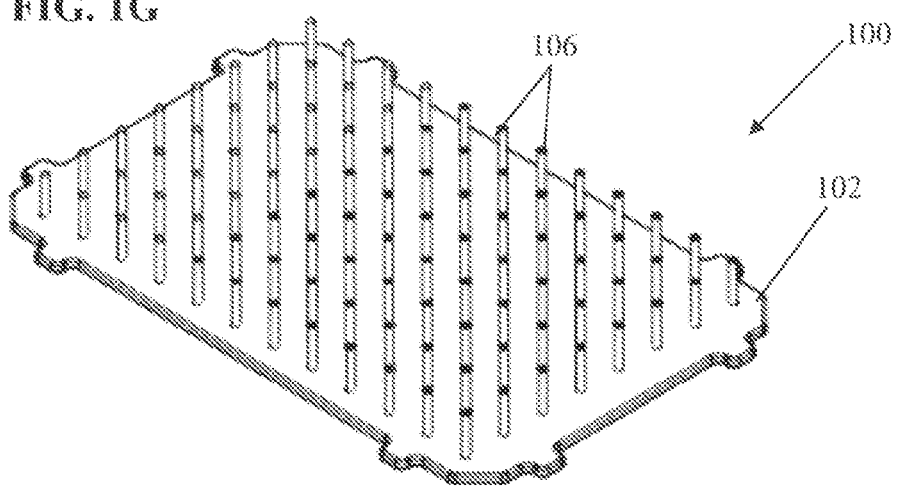

FIGS. 1E-G show an ice nucleating device configured as a removable insert for a multiwell plate, in accordance with an illustrative embodiment of the invention. Referring to FIG. 1E, a top view of an ice nucleating device insert 100 is shown. Ice nucleating device insert 100 includes a base 102 that supports a plurality of protrusions 106. Protrusions 106 can be integral with base 102 or protrusions 106 can separate from base 102 and configured for insertion into the base 102. In some embodiments, protrusions 106 can be partitioned into two or more zones 104, 104', 104". For example, when an insert includes two or more different types of protrusions, the different types of protrusions can be segregated into different zones. In some embodiments, when multiple types of protrusions are used, they can be arranged randomly or in repeating patterns. In addition, one or more protrusions can be omitted such that when the insert is placed on the multiwell plate, the corresponding wells have no protrusion.

FIG. 1F shows a side view of an ice nucleating device insert 100, and Figure G shows a perspective view of an ice nucleating device insert 100, in accordance with an illustrative embodiment of the invention.

Figure 1I:
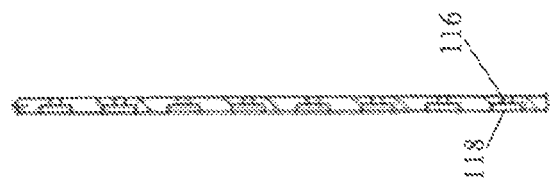
FIGS. 1H and 1I show a multiwell plate insert for receiving a plurality of ice nucleating devices, in accordance with an illustrative embodiment of the invention.
Figure 1H:
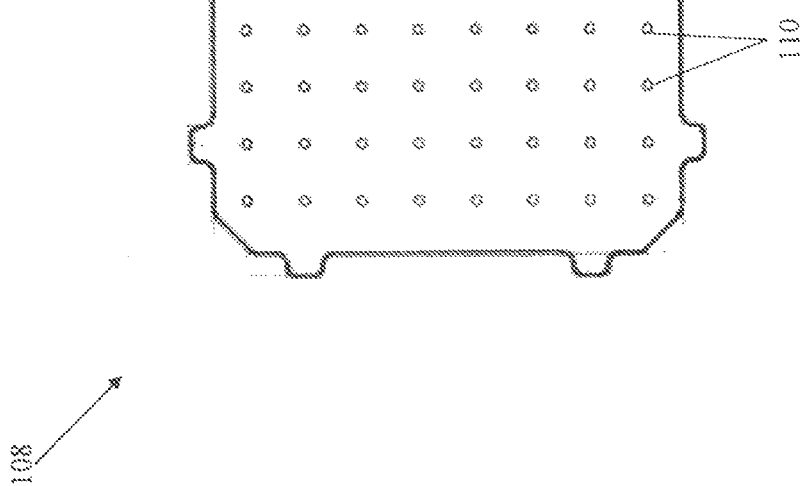

FIGS. 1H and 1I show an ice nucleating device base 108 configured as a removable insert for a multiwell plate, in accordance with an illustrative embodiment of the invention. Referring to FIG. 1H, the base 108 contains a plurality of through-holes 110 for receiving protrusions. The insert base 108 shown in FIGS. 1H and 1I is dimensioned such that it can be removeably inserted into a 96 well plate. As will be appreciated, the embodiment shown is for illustrative purposes only, and the dimensions of the insert readily can be configured for use with multiwell plates of any size. Referring to FIG. 1I, a cross-section through plane A-A in FIG. 1H is shown. In this embodiment, insert base 108 includes through-holes 110 for receiving protrusions. Through-holes 110 have a first, narrower diameter through which the protrusion fits, and a second wider diameter for engaging a base on each protrusion. Thus, in this embodiment, protrusions are inserted from the opposite side of the insert from which they project. In some embodiments, recesses are used rather than through-holes for receiving protrusion bases.

In some embodiments, the insert is made of the same material as the multiwell plate, for example a plastic such as polystyrene, polycarbonate, or acrylic. The thickness of the insert base will vary depending on the construction material. In some embodiments, the thickness of the insert is, for example, about 0.1 mm to about 10 mm, more preferably about 1 mm to about 3 mm, and more preferably still about 2 mm. It will be readily appreciated that the foregoing dimensions are illustrative only and that any suitable dimensions and configurations can be used without departing from the scope of the invention.

In addition, protrusions can be made of any suitable material, and can be made out of the same material as the base for ease of manufacture. In a preferred embodiment, the protrusions are made of a plastic such as polystyrene.

Figure 1J:
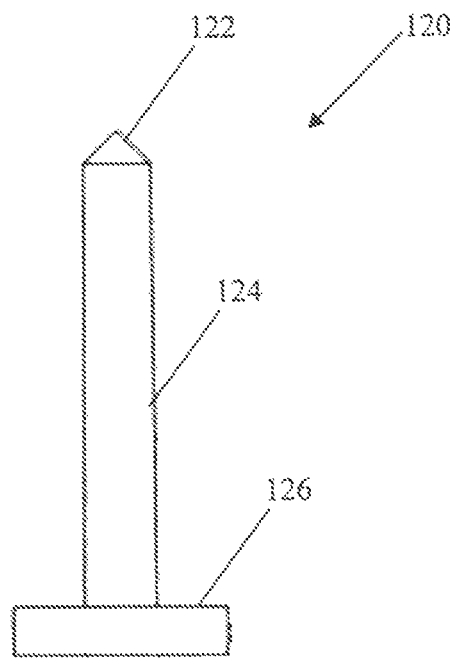
FIGS. 1J and 1K show an ice nucleating device having a single cone-shaped point, in accordance with an illustrative embodiment of the invention.
Figure 1K:
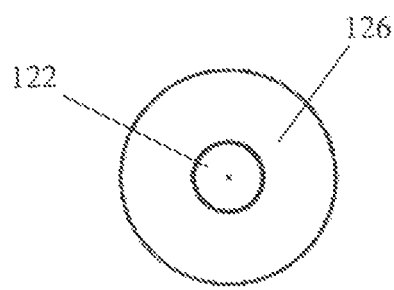
Figure 1L:
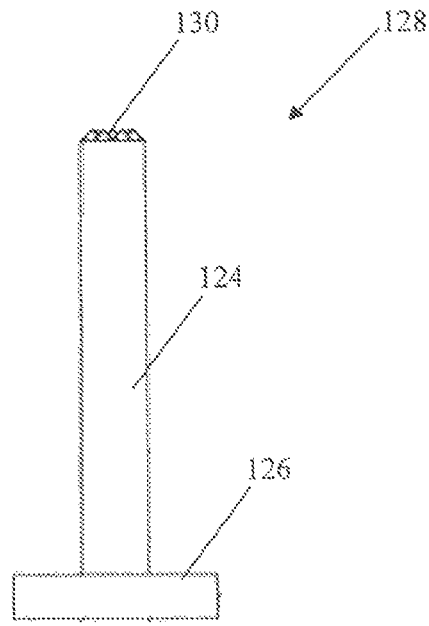
FIGS. 1L-1P show an ice nucleating device having a plurality of cone-shaped points, in accordance with an illustrative embodiment of the invention.

FIG. 1J, shows a side-view of an ice nucleating protrusion 120 having a single cone-shaped point 122, in accordance with an illustrative embodiment of the invention. Protrusion 120 has a first end forming a cone-shaped point 122, a second end forming a base 126, and a stem 124 connecting the first end and the second end. Stem 124 is long enough to contact fluid in the well of the vessel (e.g., a well of a multiwell plate). As will be appreciated, the length and width of stem 124 can vary without departing from the scope and spirit of the invention. In a preferred embodiment for use with 96 well plates, stem 124 has a length of about 5 to about 15 mm, and more preferably about 10 mm. In some embodiments, stem 124 is substantially columnar in shape and has a diameter of about 1 mm to about 2 mm, and more preferably about 1.5 mm, however any suitable shape can be used. In some embodiments, the cone-shaped point 122 can have a height of about 0.25 mm to about 1 mm, and more preferably about 0.67 mm, and the cone can have a sharp point. FIG. 1K shows a top view of protrusion 120. It will be readily appreciated that the foregoing dimensions are illustrative only and that any suitable dimensions and configurations can be used without departing from the scope of the invention.

In various embodiments, ice nucleating protrusions can have a base for engaging or securing the protrusion in a base insert. Referring again to FIG. 1J, protrusion 120 has a base 126 that is wider than stem 124. In a preferred embodiment, base 126 has a diameter of about 3 mm to about 7 mm, and more preferably about 4.5 mm. Thus, stem 124 passes through the first, smaller diameter of through-hole 110 in insert base 108 (FIG. 1I) and base 126 is received by the second, large diameter of through-hole 110. Protrusion base 126 can be secured in through-holes 110 or recesses by press fit, snap fit, adhesive, welding (e.g., sonic welding), or any other suitable fastening mechanisms. In some embodiments, there is no widened base 126 and the second end of the protrusion is substantially the same diameter as the stem 124. It will be readily appreciated that the foregoing dimensions are illustrative only and that any suitable dimensions and configurations can be used without departing from the scope of the invention.

Figure 1M:
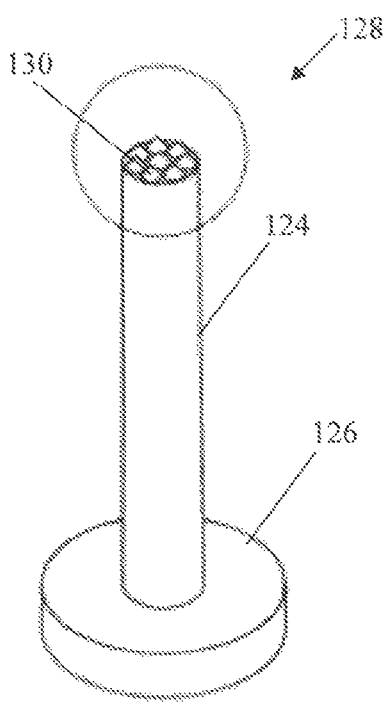
Figure 1N:
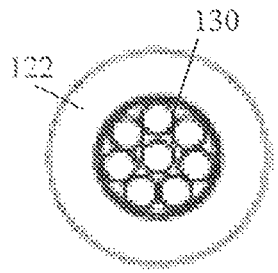
Figure 1P:
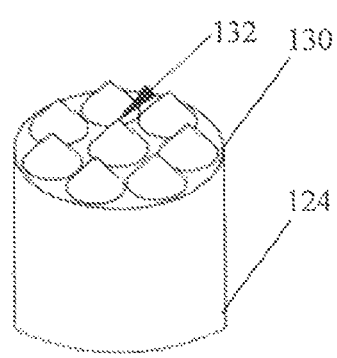
Figure 1O:
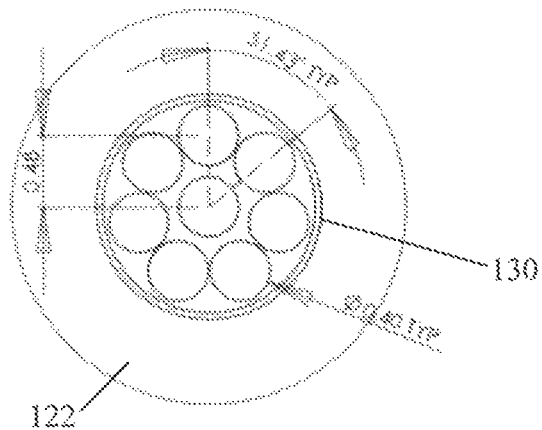

FIGS. 1L to 1P show an ice nucleating protrusion 128 having a plurality of cone-shaped points 130, in accordance with an illustrative embodiment of the invention. Referring to FIG. 1, which shows a side view of protrusion 128, the plurality of cone-shaped points 130 can have a height of about 0.1 mm to about 1 mm, and more preferably about 0.25 mm. Any number of cone-shaped points can be included, such as for example, between about 2 points and about 50 points, and more preferably between about 5 points and about 15 points, and more preferably still about 7 points to 9 points. In some embodiments, one or more cones have sharp points. In FIGS. 1M-P, an 8 point embodiment is shown with a cone-shaped point in the center encircled by 7 cone-shaped points. As shown in FIG. 1O, the cone-shaped points 130 are spaced about 0.48 mm from peak to peak and at an arc of about 51.43 degrees from peak to peak relative to the center cone-shaped point. It will be readily appreciated that the foregoing dimensions are illustrative only and that any suitable dimensions and configurations can be used without departing from the scope of the invention.

FIG. 1M shows a perspective view of protrusion 128, and FIG. 1O shows a close-up perspective view of the first end of protrusion 128. FIG. 1N shows a top view of protrusion 128.

Figure 1Q:
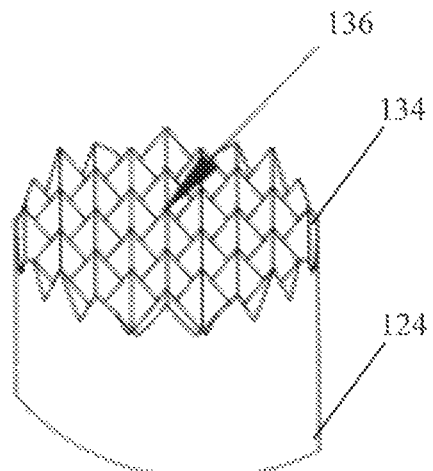
FIGS. 1Q and 1R show an ice nucleating device having a plurality of pyramid-shaped points, in accordance with an illustrative embodiment of the invention.
Figure 1R:
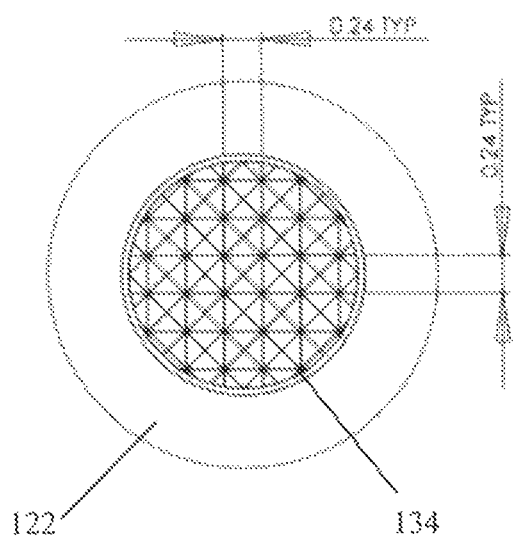

FIGS. 1Q and 1R show a protrusion 134 having a plurality of pyramid-shaped points 136. The plurality of pyramid-shaped points 136 can have a height of about 0.1 mm to about 1 mm, and more preferably about 0.25 mm. Any number of pyramid-shaped points 136 can be included, such as for example, between about 2 points and about 50 points, and more preferably between about 20 points and about 40 points. In some embodiments, the pyramids have sharp points. Referring to FIG. 1R, in some embodiments the pyramid-shaped points 136 are spaced about 0.24 mm from peak to peak and about 0.24 mm from trough to trough. It will be readily appreciated that the foregoing dimensions are illustrative only and that any suitable dimensions and configurations can be used without departing from the scope of the invention.

As will be appreciated, any suitable shape can be used for the point or points of a protrusion. Where multiple points are used the points can be the same shape or different shapes, and the points can be evenly spaced or randomly spaced and arranged randomly or in a pattern.

In some embodiments, the base or cover has no through-holes or recesses and the ice nucleating protrusions are joined directly to the base or cover. In some embodiments, the base or cover and the ice nucleating protrusions are manufactured (e.g., molded or machined) as a single integral unit.

Figure 2A:
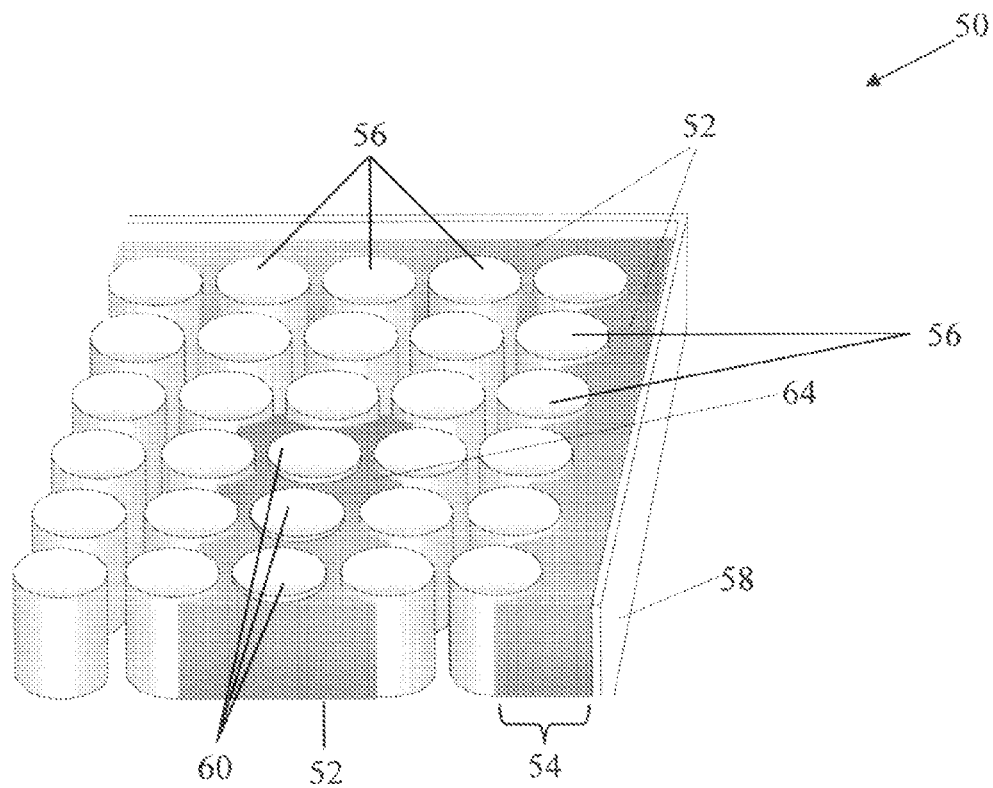
FIGS. 2A-B show cross-sectional views of an insulated vessel, in accordance with an illustrative embodiment of the invention.

In preferred embodiments, the vessel is a multiwell plate 50 which has been insulated to promote even cooling between exterior (i.e., outer) and interior (i.e., inner) wells during cryopreservation. Referring to FIG. 2A, insulating material 52 is applied to the free space 54 between the exterior wells 56 and the outer wall 58 of the multiwell plate 50 such that a portion of the free space 52 in the periphery of the multiwell plate 50 is filled with insulating material 52. In some embodiments, the insulting material 52 fills substantially all of the free space 54 between the exterior wells 56 and the outer wall 58 of the multiwell plate 50. Insulating material can also be applied to some or all of the free space between two or more exterior wells 56. Insulating material can also be applied to some or all of the free space 64 between two or more interior wells 60 of the multiwell plate. In some embodiments, insulating material 52 is applied to the underside of a multiwell plate 50 where the free space 52 is accessible.

In some embodiments, the insulating material is applied such that it fills some or all of the free space surrounding one or more wells of a multiwell plate. In another embodiment, the insulating material is part of, or occupies part of, each well of the multiwell plate. In yet another embodiment, the insulating material surrounds the exterior or interior wells, and/or occupies the interior of at least one well or vessel.

Figure 2B:
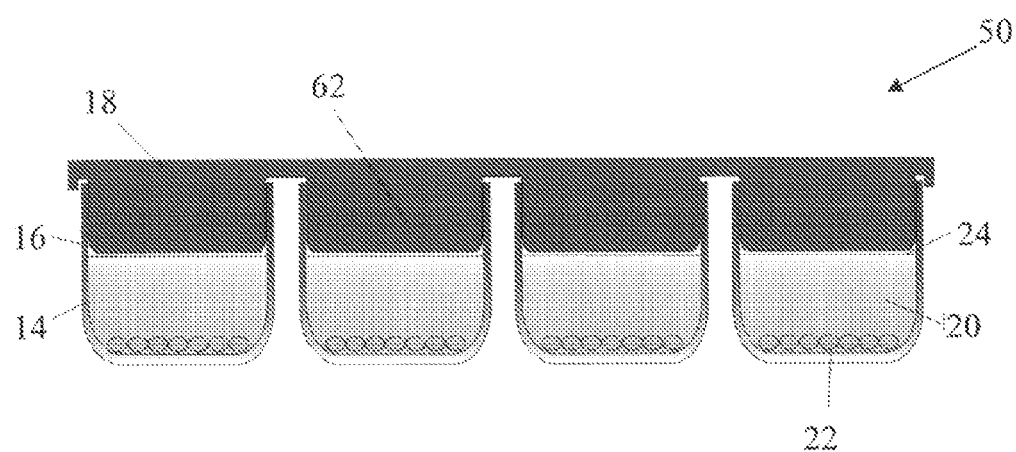

Referring to FIG. 2B, the insulating material 62 can be attached to or integral with the lid 18 of the vessel, and the insulating material can be configured to occupy some or all of the vessel's interior above the fluid line 24 of the fluid overlay 20.

In a preferred embodiment, the insulation material is the same material utilized in the tissue culture plate such as, for example, acrylic, polycarbonate and polystyrene. Using the same material is advantageous for ease of manufacturing. In some embodiments, the insulating material can consist of a specific insulating material such as acrylic caulk, weather stripping, hot glue, and other forms of insulating material including but not limited to caulk, foams, sprays, or sheets. The insulating material can be attached to or integral with the vessel, or the insulating material can be detachable from the vessel.

The present invention overcomes the previous limitations by providing an apparatus, method, and composition for the production of frozen ready to use cell cultures for diagnostic assays, comprising the steps of providing cells, and a substrate selected from the group consisting of glass and plastic; placing the cells on the substrate under conditions such that the cells are attached to the substrate to produce a cell monolayer; and freezing the cell monolayer under conditions such that the cell monolayer remains intact and attached to the substrate and is viable upon thawing. In the preferred embodiment, the substrate is the plastic comprising the well of a multiwell plate. In still further embodiments, the substrate is glass. However, it is not intended that the present invention be limited to any particular substrate. Furthermore, while attached cell monolayers are preferred, the invention is not limited to cell monolayers. The invention can also be used to cryopreserve other complex cellular structures, such as tissues and organs.

One embodiment of the present invention provides a container system to promote and initiate the nucleation of ice. In order to successfully freeze biological materials in a reproducible manner, it is common practice to cool the materials to a temperature below the melting point thereof, then after a short period of thermal equilibration, to nucleate ice in the supercooled material. In the present embodiment, the container is a multiwell tissue culture plate where a disposable and removable insert having a needle-like protrusion would be suspended in the media within each of the culture wells; in some embodiments, the well is a vial (cryovial); the insert can contain a single sterile protrusion or many protrusions having one or more nucleating sites whereby the liquid media comes in contact with the ice nucleating device. In preferred embodiments, the ice nucleating device is part of a container which contains a disposable and removable insert; the insert can comprise one or more ice-nucleating structures (i.e., protrusions) extending from the lid of the tissue culture plate into the media surrounding the cell culture. The ice nucleating protrusions are preferentially made from plastic, however it is not intended that the present invention be limited to any particular material. In further embodiments, the ice nucleating device would comprise one or more ice-nucleating protrusions extending from the sides or bottom of the wells of the tissue culture plate into the media surrounding the cell culture.

Once thawed, the removable insert containing the ice nucleating device can be removed. Another embodiment of the present invention provides a container with a media composition for effective cryopreservation of cells and tissues. The preservation media is a nutrient solution which can be protein-free and sera-free and can be adapted for cellular and tissue cryopreservation. The cryogenic preservation solution is preferentially CRYOSTOR™ (BioLife Solutions, Inc., Bothell, Wash.). While CRYOSTOR™ is the preferred embodiment combined with DMSO as an optimal cryoprotective agent, other cryoprotective agents can be used comprising of one or more selected from the group consisting of sucrose, trehalose, lactose, glucose, DMSO, propylene glycol, ethylene glycol, a dextran, glycerol, hydroxyethyl starch, polyvinyl pyrrolidine, formamide, 1-2-propanediol, ethanol, methanol, and polyethylene glycol.

The present invention also provides methods for the production of attached, frozen, ready-to-use cell monolayers comprising the steps of: 1) providing cells and a multiwell tissue culture plate, which can optionally include the aforementioned insulating material surrounding the exterior of any wells and/or occupying some portion of the interior of any wells; 2) placing the cells on the selected multiwell tissue culture plate under conditions such that the cells are attached to the substrate to produce a cell monolayer; 3) the cell culture media is replaced with a protein-free and serum-free cryopreservation medium under sterile conditions, the preferred biopreservation media being CRYOSTOR™; 4) the aforementioned ice nucleating device present as incorporated in any of the aforementioned descriptions; 5) the entire container is then placed in a vacuum sealed air-tight package; 6) the sealed plate is then placed and enclosed in a Styrofoam® container, which provides a reasonably consistent and reproducible rate of cooling. It is not intended that the container be vacuum sealed. It is also not intended that the container be limited to Styrofoam®, however, as any container providing a controlled rate of temperature reduction can be utilized. In some embodiments, the Styrofoam container can include isopropyl alcohol which the plates are bathed in while cooling, and the isopropyl bath can be pre-chilled to about 0 to $-10°$ C. before adding the multiwell tissue culture plate. In preferred methods, the multiwell tissue culture plates are incubated at about $4°$ C. for about 10 minutes, before the plates are transferred to $-80°$ C. for storage.

Once in the container, the entire apparatus is placed directly into a freezer preferably set at a temperature of $-80°$ C.; the temperature of the sample is then reduced at a rate near $1-2°$ C./minute although variations of the cooling rate can be used; when the preservation media temperature reaches a temperature within the preferred range of $-5$ to $-10°$ C., uniform ice-nucleation occurs; the temperature of the culture then continues to cool to the designated temperature of the freezer; the preferred end temperature is $-80°$ C., but it is not intended that the present method be limited to this temperature; once frozen, the cell cultures can be stored indefinitely, although the preferred storage time would be 1 day to 1 year. When needed for use, the cell cultures are removed from the freezer and preferably thawed by immersing the entire package in a liquid bath with a temperature of $37°$ C.; however in some embodiments, the invention can be thawed in an apparatus without liquid. In certain embodiments, the apparatus is a cell culture incubator with a temperature of $37°$ C.; while the preferred temperature is $37°$ C., the invention is not limited to an exact temperature of $37°$ C.; once thawed, the ice nucleating device is removed; the insulating material can be removed if possible but removal is not required; the cryopreservation medium is removed and replenished with cell culture growth media; whereby under the combined conditions results in a cell monolayer that remains attached to the substrate with minimal loss of viability and function when compared to the starting material.

In another embodiment, the sealed plates can be transferred to a $-20°$ C. freezer following the 10 minute incubation at about $4°$ C. The sealed plates are then incubated for about 15 minutes at about $-20°$ C. and then transferred directly into a $-80°$ C. freezer. In this embodiment of the freezing method, no styrofoam cooler/alcohol bath is used. The sealed plates remain in the $-80$ C freezer for storage. In yet another embodiment, the sealed plates can be transferred to an automated controlled rate cooling device. In this method, the plates can be transferred following the 10 minute incubation at about $4°$ C. to a pre-cooled chamber at about $4°$ C. Alternatively, the plates can be transferred directly to the chamber without prior incubation at about $4°$ C. Once the plates are placed into the chamber, a preset cooling rate can be run to freeze the plates. Once the temperature reaches about $-80°$ C. in the chamber, the plate can be transferred to a $-80°$ C. freezer for storage.

For the present invention, the preferred method incorporates the combination of the CRYOSTOR™ cryopreservation media, the ice nucleating device, and optionally the insulating material. This unique combination which is unlike the methods currently available provides the cell monolayer with a serum-free, protein free solution optimized for storage of cells at sub-zero (frozen) temperatures and a means of controlling and promoting uniform nucleation of ice near the melting point of the fluid; the combined method creates an optimal circumstance that allows for cryopreservation and exceeds in the cryopreservation process by allowing uniform cell density and viability from well to well of a multiwell plate following the cryopreservation process, and improved overall post-thaw viability and function. Levels of post-thaw viability and function are dependent upon the freezing method applied and the cell type used. Once the combined cryopreservation medium and ice-nucleating device are added to the cell monolayer following the preferred method, the apparatus would be vacuum sealed using standard technique to provide optimal freezing and storage conditions. The sealed apparatus can then be placed into a container such that the apparatus does not come in direct contact with the freezing element; the apparatus can be completely enclosed within the container; the container can provide some insulation such that the temperature of the fluid in the apparatus is reduced at a controlled rate. An example of such could be a container made of Styrofoam® foam. The container with the apparatus can then be placed into a freezer or freezing device; the preferred freezing device reaches an end temperature between −70° C. to −90° C.; while preferred, the present method is not limited to this temperature range. Under the present conditions, ice-nucleation within the apparatus typically occurs when the media temperature within the wells reaches −5 to −10° C. and ice-nucleation from well to well over the entire multiwell plate will be uniform. Once frozen, the cell monolayer can be maintained in such a state until required for use. In the preferred embodiment, the cryopreserved monolayer could be stored for 1 day to 1 year.

Upon use, the cryopreserved apparatus can be removed from the freezer or freezing device and submerged in a liquid bath; in the preferred method the bath would be water maintained at a temperature near 37° C.; the temperature is not limited to 37° C., but to achieve optimal post-thaw viability and function the temperature should be kept between 25-40° C. While this is the preferred method, additional methods can be applied such that the apparatus is placed in a dry environment like an incubator or heating block. Optimal thawing rates are best achieved if the entire outer surface area of the apparatus can be exposed to the thawing mechanism. In the preferred embodiment, the thawed multiwell apparatus would be removed from the sealed container, the mechanical ice nucleating device removed, and the cryopreservation media removed and replaced with standard culture medium. These steps can be performed under sterile or non-sterile conditions. The thawed monolayers can be used for testing and evaluation at any time thereafter.

The present invention overcomes previous limitations in the field by providing an apparatus, related method, and composition that results in uniform freezing of the cell monolayers consistently across the entire multiwell tissue culture plate and potentially providing improved post-thaw cell viability and function, which in some cell types may be comparable to that of non-frozen monolayers. Specifically, the present invention improves upon previous inventions by including both an insulating material to aid consistent well to well cooling and warming and a mechanical device to control ice-nucleation during the freezing process. Furthermore, the present invention includes the use of a unique protein-free and serum-free preservation medium designed specifically for maintenance, protection, and storage of cells held in a frozen state. Additionally, the combination of the insulating material and mechanical ice nucleating device along with the CRYOSTOR™ cryopreservation media provides for an optimal preservation environment and homogeneous ice-nucleation resulting in improved viability and function of the cell monolayer. Finally, the present invention overcomes the limitations of previous inventions by providing specific and simplified method for the freezing, storage and thawing of cell monolayers for ready-to-use formats.

The following examples are provided for illustration, not limitation.

EXAMPLE 1

Cooling Profile of Interior and Exterior Wells of a 96-Well Plates and the Effects of an Insulating Material In this example, 96-well tissue culture plates were used to investigate the differences in cooling rate between interior and exterior wells and the efficacy of including an insulating material. For this example, the insulating material was applied to the outer underside edge of the exterior wells as demonstrated in FIG. 2A. To insulate plates, standard clear acrylic latex caulk plus silicone was applied to the underside exterior wells of the 96-well tissue culture plates previously described. Caulk was applied into the outside gap found between the exterior wells and the outer plate edge of the tissue culture plates (see FIG. 2A). Caulk was applied with a standard caulk gun. The caulk was added to the exterior well gaps until any obvious air space was filled. The excess caulk was wiped away and leveled off so that the caulk insulating layer was flush with the plate well bottoms. Plates were then left overnight so that the caulk could set. Once prepared, plates were tested as described to determine insulation efficacy.

Plates without an insulating material were tested to compare the results and efficacy of the insulating material. After the insulating material was added, 80 μl of culture media was added to each well. A thermocouple was attached to the inside of a centrally located interior well and another thermocouple was attached to the inside of an exterior well. The tips of the thermocouples were immersed in the liquid culture media but did not touch the well surface. The lid was placed on the plates and the plates were then placed into a −80° C. freezer. Temperature readings were collected over a time period of 0-30 minutes.

Figure 3:
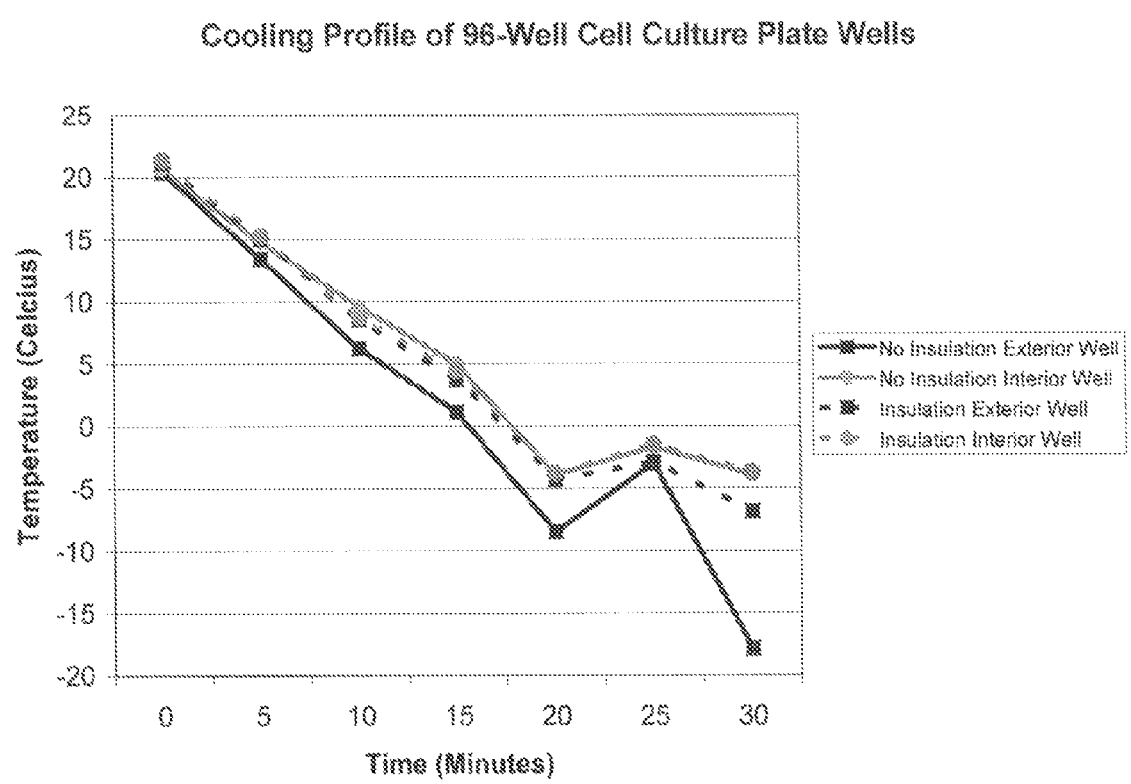
FIG. 3 is a graph showing the differences in cooling rates of interior and exterior wells of a 96-well tissue culture plate with and without the addition of an insulating material, in accordance with an illustrative embodiment of the invention.

As shown in FIG. 3, the inclusion of an insulating material effectively reduces the variability in cooling rates observed between the interior and exterior culture wells of the 96-well plate. Without the inclusion of an insulating material, exterior wells cooled at a much faster rate as compared to interior wells. Using the cooling process, exterior wells not having an insulating material reached a temperature of −8.5° C. after 20 minutes, while the interior well had only reached −3.8° C. This range in temperature differences could significantly affect the ice-nucleation events from well to well. Exterior wells typically have ice nucleation events at an earlier time point compared to interior wells. The significant differences in temperature from well to well relate directly to differences observed in post-thaw cell recovery and viability. When exterior wells were surrounded with the addition of an insulating material, cooling rates much more closely resembled the cooling rate of the interior wells. After 20 minutes, the temperature of the exterior well with an insulating material was at −4.3° C., while the temperature of the interior well was at −3.8° C. The results of this series of experiments demonstrate the feasibility and efficacy of using an insulating material to aid in improving the consistency of well to well cooling and eventual ice-nucleation.

EXAMPLE 2

Freezing of NHDF Cell Monolayers in 96-Well Plate Testing Different Cryopreservation Media and Freezing Methods In this example, different cryopreservation media were investigated as models to cryopreserve NHDF, normal human dermal fibroblast, cell monolayers in multiwell plates following three separate freezing methods. NHDF cells were cultured and subsequently plated at an equal number of cells/well in a 96-well culture plate (BD Falcon). The cultures were left undisturbed for one day to achieve confluent attached cell monolayers. Prior to preparing the cultures for preservation, an initial assessment of the metabolic activity was performed to determine cell viability prior to freezing. alamarBlue® (TREK Diagnostic Systems) was utilized to assess cell viability.

alamarBlue® is soluble, stable in culture medium and is non-toxic. The continuous monitoring of cells in culture is therefore permitted. Specifically, alamarBlue® does not alter the viability of cells cultured for various times as compared to assessment by trypan blue exclusion. Because alamarBlue® is non-toxic, the cells under study can be returned to culture or used for other purposes including histological studies. Proliferation measurements with alamarBlue® can be made by using either spectrophotometry or fluorometry to monitor the absorption of alamarBlue® supplemented cell culture media at two wavelengths.

To perform the assay, alamarBlue® was used according to manufacturer instructions. Briefly, cell culture media was removed from the wells and alamarBlue® was added (100 µl/well) to each well and incubated at 37° C. for 1 hour. Following the incubation, the plates were analyzed with a fluorescent microplate reader (Tecan; Infinite 200 model) with an excitation at 530-560 nm and emission at 590 nm. The Magellan™ software (Tecan, Switzerland) is used in combination with Infinite 200 fluorescent microplate reader for fluorescent data acquisition. Relative fluorescent units for pre-freeze cell monolayers were set to 100% (Control) and the experimental conditions are compared to the pre-freeze control.

In order to assess the data and efficacy of each experiment, the raw fluorescent values were collected via a fluorescent plate reader. The raw fluorescent values or relative fluorescent units were collected for each well of the 96-well plate. For each study/experiment, the relative fluorescent units were used to determine relative cell viability (per manufacturer's (TREK Diagnostic Systems') product materials). For the current studies, the relative fluorescent units collected for the various experimental conditions tested were compared to non-frozen (37° C. control) plated cells. Typically, an average relative fluorescence of at least 6 wells of a 96-well plate was determined (more depending on the condition tested). The average numbers of the experimental conditions were then compared to the control non-frozen average and a percentage was determined. The variability observed between each of the tested wells for each experimental was expressed as either the percent error or standard deviation (performed with Excel software).

Following the pre-freeze viability assessment, the alamarBlue® was removed and the various cryopreservation media were added. Four different cryopreservation media conditions were tested: NHDF complete cell culture media+5% DMSO (Media 5%), NHDF complete cell culture media+ 10% DMSO (Media 10%), CRYOSTOR™+5% DMSO (CS5), and CRYOSTOR™+10% DMSO (CS10). The 96-well plate was divided into 4 quadrants consisting of 24 wells in each. 80 µl/well of the respective cryopreservation media was added to each 24-well quadrant. No ice nucleating device was used. The 96-well plate was then placed into a Ziploc® bag and sealed. The sealed plate was then placed at 2-8° C. for 10 minutes prior to freezing. After 10 minutes, plates were subject to freezing via three separate methods: (1) Alcohol bath method—The sealed plate was then placed into a Styrofoam box and the entire container was then put into a −80° C. freezer. The wells were then visualized for seeding events (ice nucleation). With this method, seeding events were noted as early as 20 minutes while the final seeding event occurred around 60 minutes post storage; (2) −80° C. freezer method—The sealed plate was transferred to a −20° C. freezer and stored for 15 minutes and then transferred directly into a −80° C. freezer and freezing continued. With this method, seeding events were noted as early as 10 minutes while the final seeding event occurred around 40 minutes post storage; (3) Controlled rate freezer method—The sealed plate was transferred to an automated control rate freezing device (Cryomed) with the chamber temperature set to 4° C. Once the plate was placed into the chamber, the temperature of the chamber was reduced 1° C./minute to a final temperature of −80° C. When the program was completed, the plate was transferred to the −80° C. freezer for storage. With this method, no seeding events were visualized since the plate was inside the chamber. The plates were kept at −80° C. for 24 hours. Plates were then removed and submerged completely in a 37° C. water bath. Within 5 minutes, all of the wells had thawed. The cryopreservation media was removed from the plate, replenished with 100 µl/well of fresh culture media, and the entire plate was placed in a 37° C. incubator to recover. Cell viability was assessed 24 hours post thaw as described previously for the pre-freeze controls.

Figure 4:
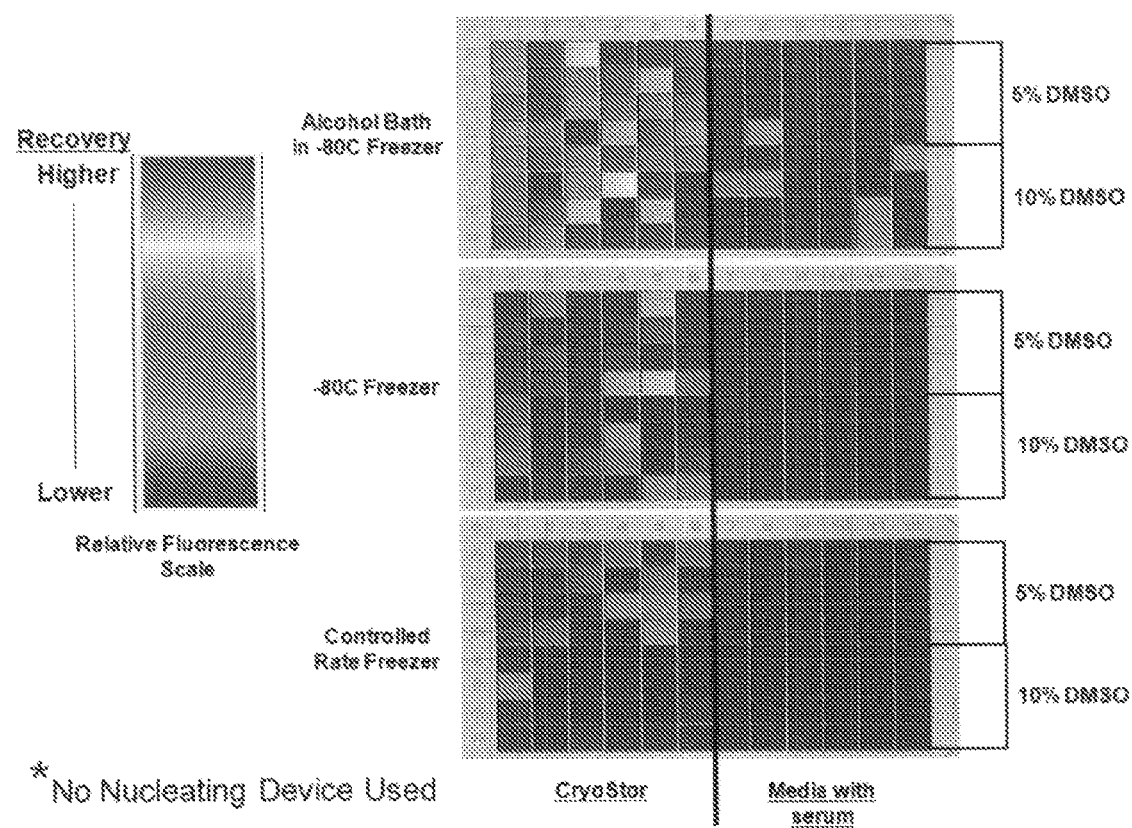
FIG. 4 is a diagram showing the relative fluorescence of Normal Human Dermal Fibroblast (NHDF) cells in each well of a 96-well tissue culture plate following freezing in either media with serum and 5% DMSO, media with serum and 10% DMSO, CRYOSTOR™ CS5 (5% DMSO), or CRYOSTOR™ CS10 (10% DMSO), in accordance with an illustrative embodiment of the invention. Three different freezing methods were investigated; (1) plates submerged in an alcohol bath in a styrofoam cooler in a −80° C. freezer, (2) −20° C. freezer then directly into a −80° C. freezer, and (3) an automated controlled rate freezing device set to −1° C./minute. No nucleating device was used.

FIG. 4 is an image obtained from the Magellan™ software used in combination with the fluorescent microplate reader. The image portrays the relative fluorescent intensity based on NHDF cell density and metabolic activity for each well as a color for all wells of the test plate. Color associated with fluorescent intensity can also be correlated to viability as depicted on FIG. 5. Relative fluorescent units for pre-freeze cell monolayers were set to 100% (Control) and the experimental conditions are compared to the pre-freeze control. Using this format, a well depicted as red has a high fluorescent intensity and a high relative viability, while a well depicted as blue has a very low associated relative viability. The overall scale is determined by the well having the highest fluorescent intensity (darker red color) and the well with the lowest overall fluorescent intensity (darker blue color). Wells having like colors have similar fluorescent intensities and similar relative viability.

As depicted in FIG. 4, the results of this experiment indicate that with each freezing method tested, the CRYOSTOR™ solutions result in the highest recovery of NHDF cells compared to the traditional media+DMSO solutions. Of the CRYOSTOR™ solutions, the CS5 results in the best recovery and these general recovery trends are consistent with results obtained with NHDF cells cryopreserved in traditional cryovial formats (suspended cells). Additionally, results indicate that the alcohol bath method provides the most optimal freezing method while the controlled rate freezer method may be the least optimal with the NHDF cell model. A high level of well to well variability is evident with each of the solutions in each of the freezing methods.

Figure 5:
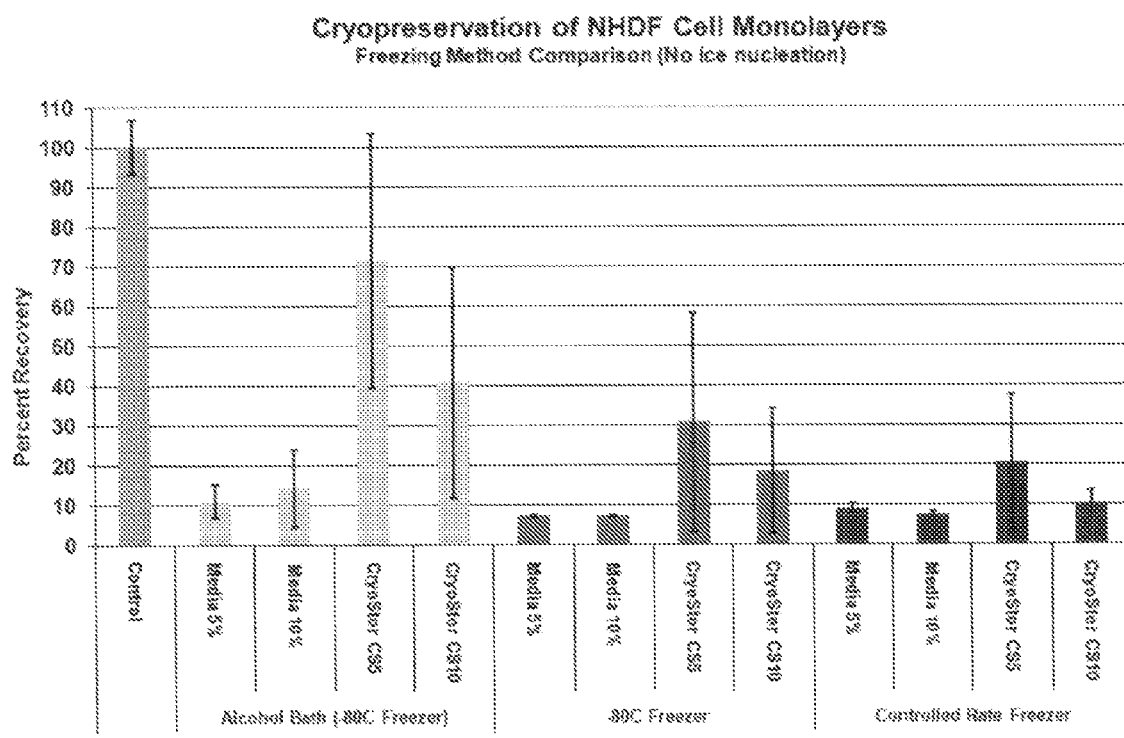
FIG. 5 is a graph showing relative percent viability of NHDF cells following freezing in each of the conditions tested in FIG. 4.

As shown in FIG. 5, the results of this experiment demonstrate that cell monolayers cryopreserved in the CRYOSTOR™ media performed significantly better than the monolayers cryopreserved with the traditional media and DMSO (CS10 and CS5 compared to Media 10% and Media 5%). Cell monolayers cryopreserved in the CS5 performed the best with 70%, 40%, and 20% viability post-thaw respectively for each of the freezing methods compared to the control, while cell monolayers cryopreserved in media and 5% DMSO resulted in less than 10% viability post-thaw in each of the freezing methods. A high level of variability in well-to-well viability was experienced in each of the conditions using CRYOSTOR™ due to the level of random ice nucleation noted during the freezing process. Essentially no variability is noticed with the media and DMSO conditions, but this is because no cells were recovered from any of the freezing methods. CRYOSTOR™ media showed the highest post-thaw viability for cryopreserving cell monolayers when compared to standard cryopreservation media.

EXAMPLE 3

Freezing of NHDF Cell Monolayers in 96-Well Plate Testing Efficacy and Variability of CRYOSTOR™ CS5 Cryopreservation Media Combined with or without an Ice Nucleating Device In this example, an ice nucleating device as described in FIG. 1 was developed and utilized to determine device utility and efficacy compared to having no ice nucleating device. For the provided examples demonstrated in FIGS. 6-9, the ice nucleating device is essentially as described in FIG. 1. The ice nucleating device was prepared from the same material as the 96-well tissue culture plates (BD Biosciences, Billerica, Mass.). Each device was cut from the culture plate material using a razor blade to a length of about 8 cm and a width of about 1 cm (the exact width and length varied slightly for each device). The devices were rectangular in shape and did not have a single pointed end. The edges were rough, resembling multiple ice nucleating points. Once the individual ice nucleating devices were prepared, a soldering device was used to melt one end of the device and allowing it to be attached to the lid of a tissue culture plate. Once cooled, the device was firmly attached to the lid and protruded from the underside of the lid as depicted in FIGS. 1A and 1B. In all, 48 ice nucleating devices were prepared and attached (1/well) making up half of an entire 96-well tissue culture plate. Each device was confirmed to penetrate the liquid fill level of the tissue culture well without touching the bottom surface of the well.

For this study, NHDF cell monolayers were utilized, and cell monolayers were prepared and formed as described in previous examples. NHDF cell monolayers were prepared for cryopreservation essentially as described in Example 2. Briefly, CRYOSTOR CS5 was added to all wells except for the 4 wells in the center of the plate. These wells received standard cell culture media with 5% DMSO as the cryopreservation solution. Following the addition of the chilled cryopreservation solution, a prototype ice nucleating device lid, described above, containing ice nucleating spikes protruding from the underside of the lid was placed on the plate. The lid contained a single ice nucleating device for each well. Half of the plate lid was designed to contain an ice nucleating device while the other half did not, which allowed for intra-experimental comparison. Each ice nucleating device was attached directly to the plate lid surface and an ice nucleating device extended into the center of each cell culture well when the lid was placed on the tissue culture plate. The ice nucleating devices were long enough to penetrate the liquid medium but did not touch the well surface or the cell monolayer.

After the lid containing the ice nucleating device was added to the plates, the plate was placed into a freezer-safe plastic bag and vacuum sealed. Plates were then subjected to a controlled freezing rate. Plates were first stored at 2-8° C. for 10 minutes and then placed into a Styrofoam foam cooling chamber at −80° C. The Styrofoam foam cooling chamber contained enough isopropyl alcohol such that the plate when placed into the chamber would be completely covered. The Styrofoam foam cooling chamber was previously chilled such that the bath temperature was around 0° C. when plates were placed into the chamber. A 1-2° C. per minute cooling rate was achieved. Plates remained in the Styrofoam foam cooling chamber for 3 hours. After 3 hours, plates were removed and stored at −80° C. for 24 hours, which was sufficient time to ensure that the media in each well froze solid. Plates were thawed using a 37° C. water bath as described previously in Example 2. Once thawed, plates were removed from the freezer-safe plastic bag. The ice nucleating device was removed from the wells along with the cryopreservation solution, and fresh cell culture media was added. The plates were then evaluated as in previous experiments. Data shown are representative of multiple experiments. The plates were evaluated using a plate reader as described in Example 2.

Figure 6:
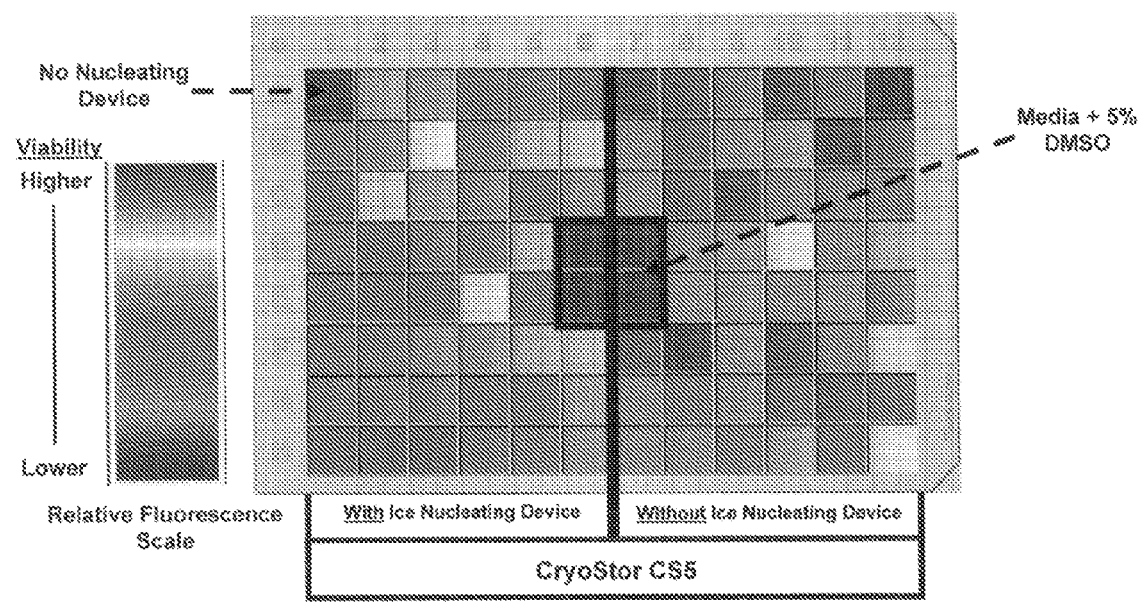
FIG. 6 is a diagram showing the relative fluorescence of Normal Human Dermal Fibroblast (NHDF) cells in each well of a 96-well tissue culture plate following freezing using CRYOSTOR™ CS5 with and without a nucleating device, in accordance with an illustrative embodiment of the invention.

FIG. 6 is an image obtained from the Magellan™ software used in combination with the fluorescent microplate reader. The image portrays the relative fluorescent intensity based on NHDF cell density and metabolic activity for each well as a color for all wells of the test plate. Color associated with fluorescent intensity can also be correlated to viability as depicted on FIG. 8. Relative fluorescent units for pre-freeze cell monolayers were set to 100% (Control) and the experimental conditions are compared to the pre-freeze control. Using this format, a well depicted as red has a high fluorescent intensity and a high relative viability, while a well depicted as blue has a very low associated relative viability. The overall scale is determined by the well having the highest fluorescent intensity (darker red color) and the well with the lowest overall fluorescent intensity (darker blue color). Wells having like colors have similar fluorescent intensities and similar relative viability.

Figure 7:
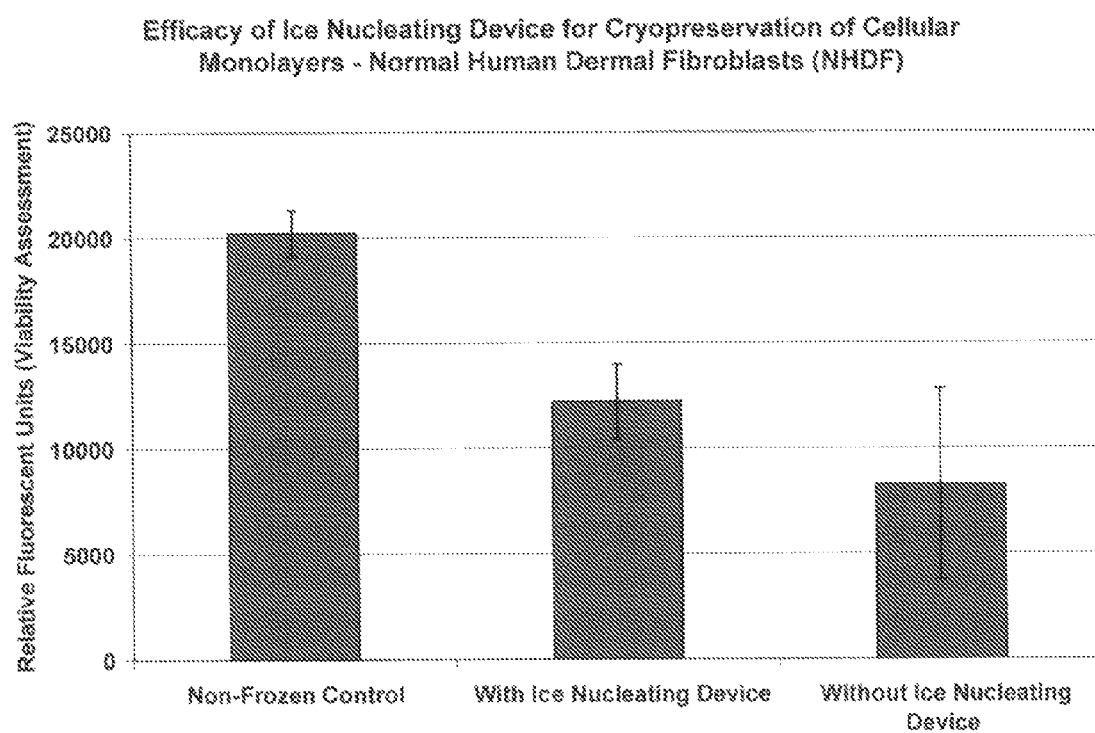
FIG. 7 is a graph showing relative fluorescence of NHDF cells following freezing using CRYOSTOR™ CS5 with and without a nucleating device, in accordance with an illustrative embodiment of the invention.

As shown in FIG. 6, the addition of the ice nucleating device effectively reduces well to well variability compared to wells not having an ice nucleating device. The wells having the ice nucleating device have a high number of wells with a very similar color range, while the wells without an ice nucleating device have a much wider range of color from one well to another. The large variation in color seen from well to well is directly correlated to the increased variability in cell density and viability from well to well observed without the presence of an ice nucleating device. It should be noted that fluorescent intensity was very low in all wells having media and 5% DMSO as the cryoprotective agent. When the relative fluorescent intensity for each of the wells is plotted on a graph as shown in FIG. 7, the drastic decrease in well to well variability using an ice nucleating device is easily observed from the lower standard deviation. In FIG. 7, the average relative fluorescent units for the respective wells is shown. To demonstrate the range in well to well variability, the standard deviation for wells having an ice nucleating device and those without an ice nucleating device is depicted. The standard deviation is significantly less for the sample wells containing the ice nucleating device as compared to the standard deviation of the sample wells without an ice nucleating device. In addition, the relative fluorescent units obtained from non-frozen control samples is averaged and shown in FIG. 7. Notably, the standard deviation of the wells with the ice nucleation device is comparable to that of the non-frozen control. Furthermore, the overall average relative fluorescent intensity for wells having an ice nucleating device is higher than that of those without an ice nucleating device. When compared to the non-preserved control, this correlates to an average of 60% viability for wells with an ice nucleating device and 40% for wells without an ice nucleating device following 1 day of recovery post-thaw. It should be noted that the overall viability obtained is cell type dependent. Well to well consistency is of significant importance to the utility of frozen cell monolayers for high throughput analysis.

EXAMPLE 4

Freezing of CHO Cell Monolayers in 96-Well Plate Testing Efficacy and Variability of CRYOSTOR™ CS5 Cryopreservation Media Combined with or without an Ice Nucleating Device (Alcohol Bath Freezing Method and Ice Nucleation Device)

In this example, an ice nucleating device as described in Example 3 was utilized to determine device utility and efficacy compared to having no ice nucleating device. For this study, Chinese Hamster Ovary (CHO) cell monolayers were utilized, and prepared and formed as described in Example 2. The plates were frozen and thawed as described in Example 2. Figures shown are representative of multiple experiments. The plates were evaluated using a plate reader as described in Example 2.

Figure 8:
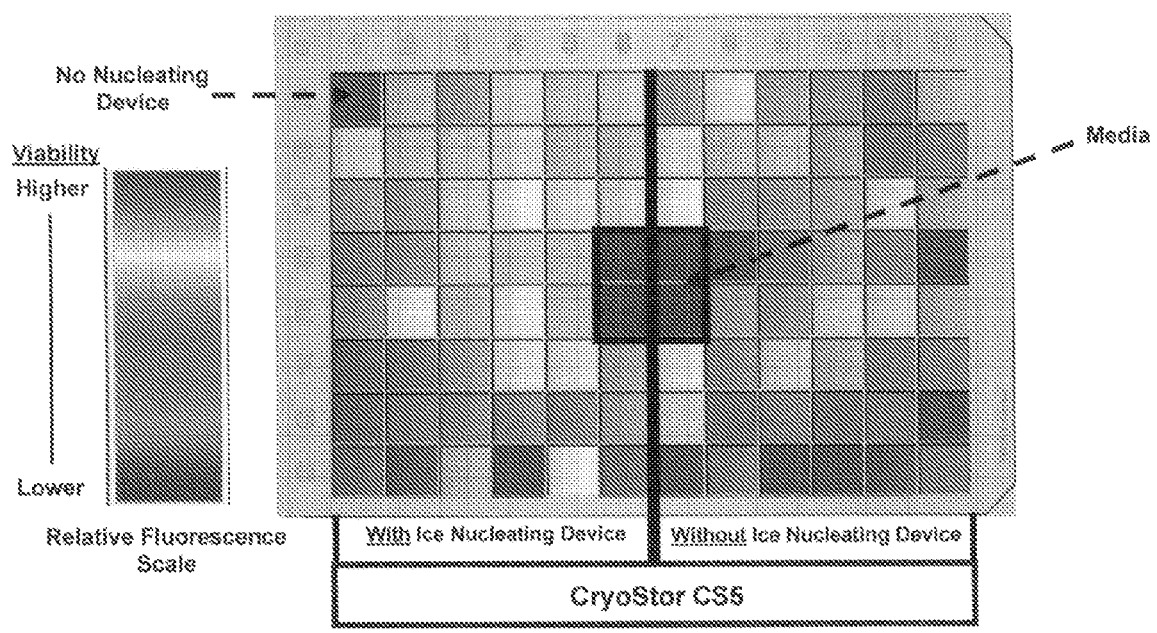
FIG. 8 is a diagram showing the relative fluorescence of Chinese Hamster Ovary (CHO) cells in each well of a 96-well tissue culture plate following freezing using CRYOSTOR™ CS5 with and without a nucleating device, in accordance with an illustrative embodiment of the invention.

FIG. 8 is an image obtained from the Magellan™ software used in combination with the fluorescent microplate reader as described in Example 3. The image portrays the relative fluorescent intensity based on CHO cell density and metabolic activity for each well as a color for all wells of the test plate. Color associated with fluorescent intensity can also be correlated to viability as depicted on FIG. 7.

Figure 9:
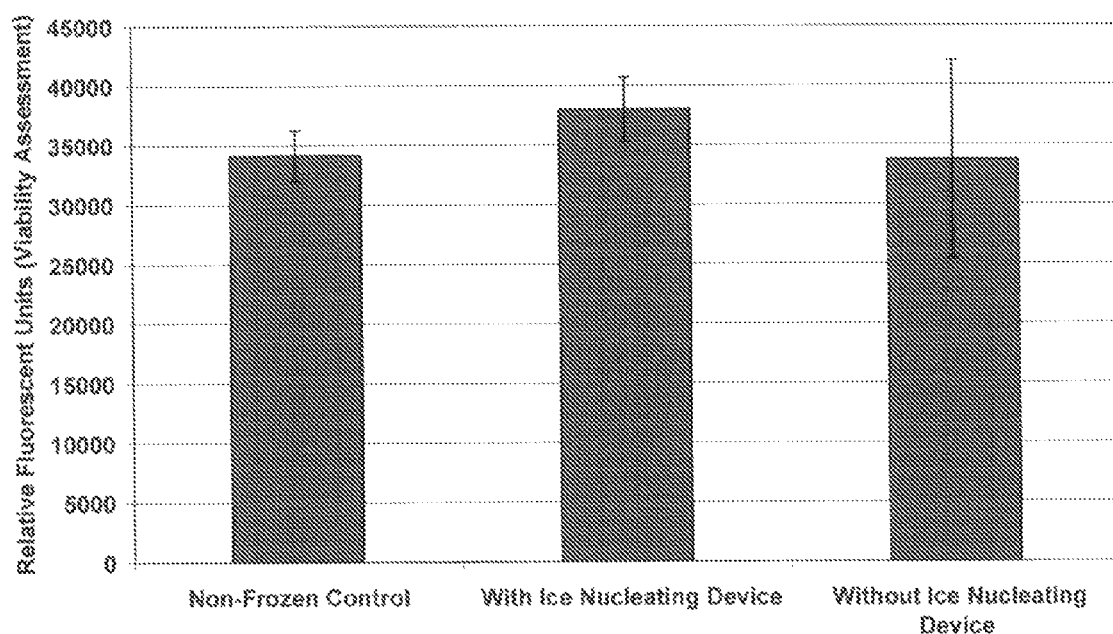
FIG. 9 is a graph showing relative fluorescence of CHO cells following freezing using CRYOSTOR™ CS5 with and without a nucleating device, in accordance with an illustrative embodiment of the invention.

As shown in FIG. 9, the addition of the ice nucleating device effectively reduces well to well variability compared to wells not having an ice nucleating device. The wells having the ice nucleating device have a high number of wells with a very similar color range, while the wells without an ice nucleating device have a much wider range of color from one well to another. The large variation in color seen in wells without an ice nucleating device is directly correlated to the increased variability in cell density and viability from well to well. When the relative fluorescent intensity for each of the wells is plotted on a graph as shown in FIG. 9, the large decrease in well to well variability using an ice nucleating device is easily observed from the lower standard deviation. In FIG. 9, the average relative fluorescent units for the respective wells is shown. To demonstrate the range in well to well variability, the standard deviation for wells having an ice nucleating device and those without an ice nucleating device is depicted. The standard deviation is significantly less for the sample wells containing the ice nucleating device as compared to the standard deviation of the sample wells without an ice nucleating device. In addition, the relative fluorescent units obtained from non-frozen control samples is averaged and shown in FIG. 9. It is important to notice that the standard deviation of the wells with the ice nucleation device is comparable to that of the non-frozen control. Furthermore, the overall average relative fluorescent intensity for wells having an ice nucleating device is higher than that of those without an ice nucleating device. When compared to the non-preserved control, this correlates to an average of 110% viability for wells with an ice nucleating device and 100% for wells without an ice nucleating device following 1 day of recovery post-thaw. The results of this example are consistent with the results described in Example 3. The addition of an ice nucleating device can significantly reduce the well to well variability compared to the cell recovery in wells without an ice nucleating device.

EXAMPLE 5

Figure 10:
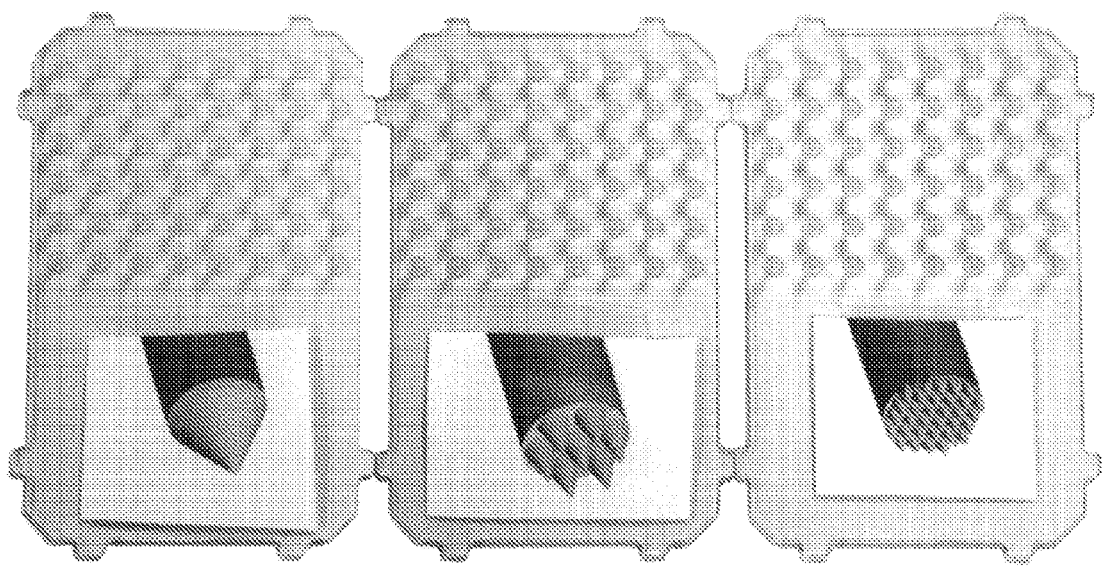
FIGS. 10A-C show perspective views of ice nucleating devices, in accordance with an illustrative embodiment of the invention.

Freezing of NHDF Cell Monolayers in 96-Well Plate Testing Efficacy and Variability of CRYOSTOR™ CS5 Cryopreservation Media or Media and DMSO Combined with or without an Ice Nucleating Device In this example, three ice nucleating device inserts as described in FIG. 10 were designed and developed and utilized to determine device utility and efficacy compared to having no ice nucleating device. For the provided examples demonstrated in FIGS. 11-16, the ice nucleating device is essentially as described in FIGS. 1E-1R and 10. The ice nucleating devices were prepared from the same polystyrene material as the 96-well tissue culture plates. Each insert device was prepared from a mold design. The devices are rectangular in shape and were manufactured having a specific ice nucleating spike design as described in FIG. 10A-C; spike design A—single cone spike, spike design B—low density array, spike design C—high density array. Ice nucleating spikes for each of the designs were manufactured so that each of the specific protrusions had equal length and width. In all, 48 ice nucleating devices were prepared making up half of an entire 96-well tissue culture plate for each design, while the other half did not have any spikes and acted as an internal control (no ice nucleating device) for each experiment. Each device was confirmed to penetrate the liquid fill level of the tissue culture well without touching the bottom surface of the well. Each of the insert devices were manufactured so that they could be used in typical standard 96-well plate formats. The devices depicted in FIG. 10 represent potential devices that could be manufactured in mass quantities.

For this study, NHDF cell monolayers were utilized, and cell monolayers were prepared and formed as described in previous examples. NHDF cell monolayers were prepared for cryopreservation essentially as described in Example 2. Briefly, CRYOSTOR CS5 was added to all wells of the bottom half of the plate, while media+5% DMSO was added to all wells in the upper half of the plate. Following the addition of the chilled cryopreservation solution, the manufactured ice nucleating device inserts, described above, were placed on the plates. The left half of the ice nucleating insert contained an ice nucleating devices while the right half did not, which allowed for intra-experimental comparison. Once the insert was placed onto the plate, the plate lid was placed on the top. The plates were then sealed and stored for 10 minutes at 2-8° C. as described in Example 3.

Figure 11:
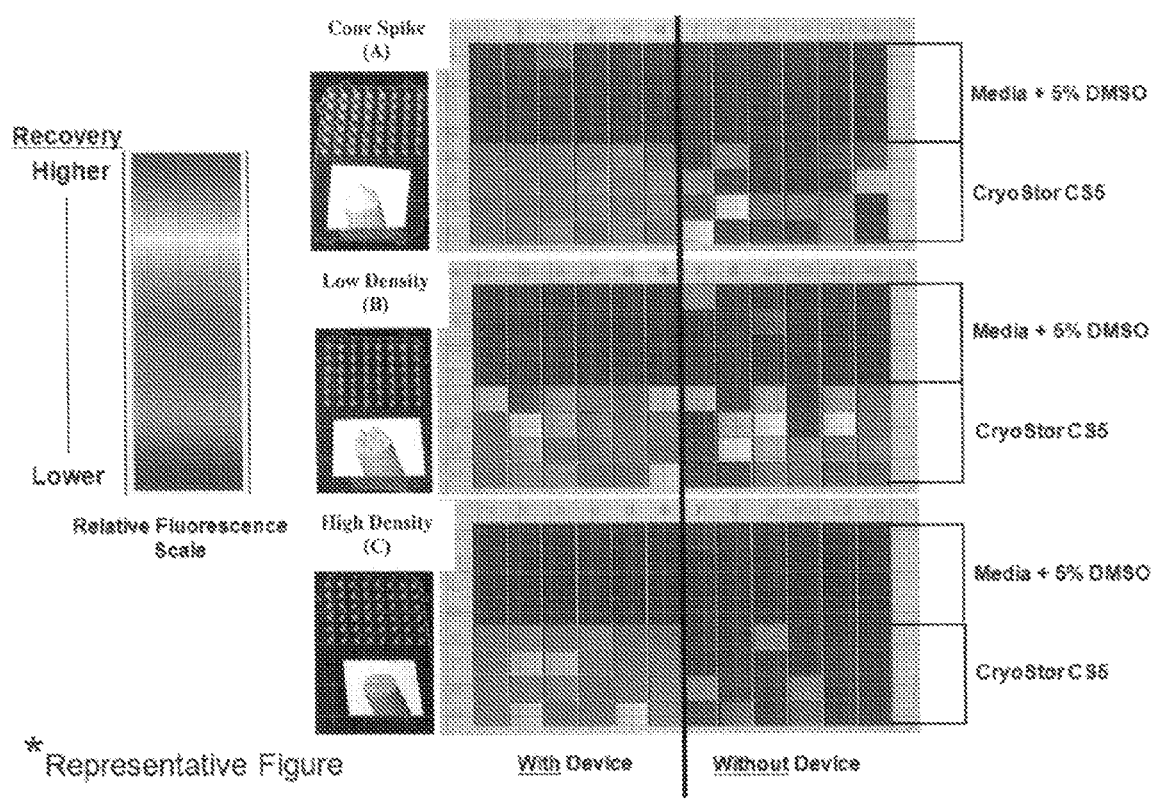
FIG. 11 is a diagram showing the relative fluorescence of Normal Human Dermal Fibroblast (NHDF) cells in each well of a 96-well tissue culture plate following freezing using the alcohol bath in a −80° C. freezing method using CRYOSTOR™ CS5 or culture media with serum and 5% DMSO with and without a nucleating device, in accordance with an illustrative embodiment of the invention.
Figure 12:
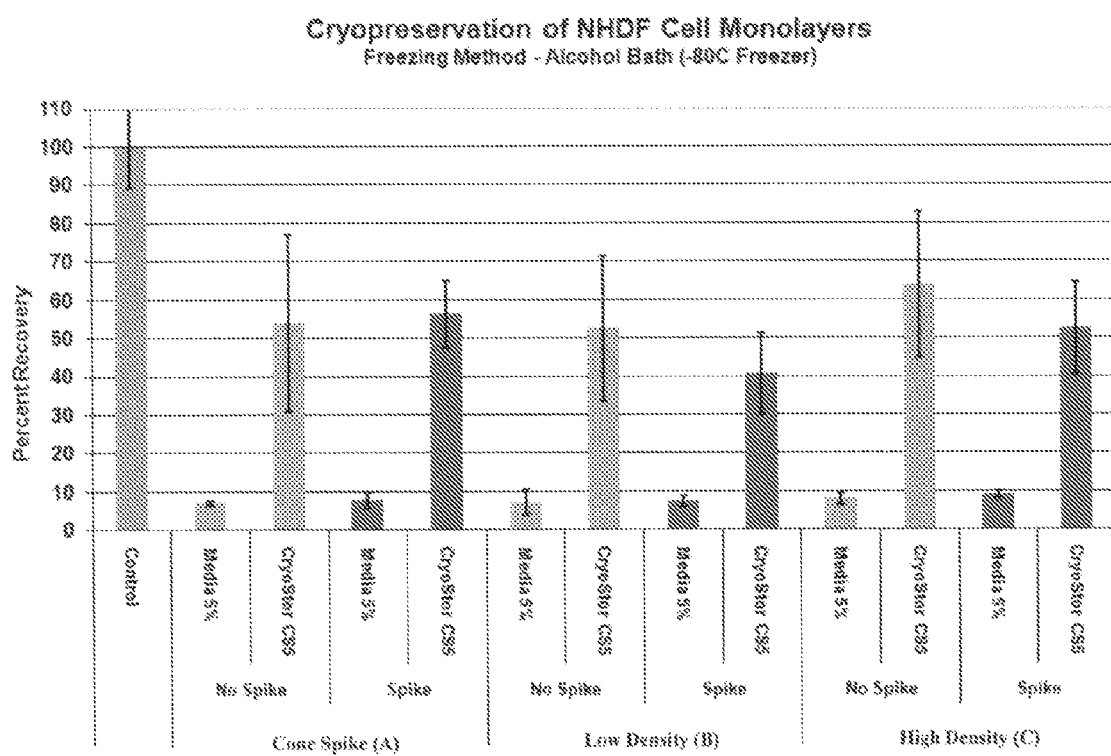
FIG. 12 is a graph showing relative percent viability of NHDF cells following freezing in each of the conditions tested in FIG. 11.

Plates were then frozen using each of the three freezing methods described in Example 2. FIGS. 11-12 were obtained using the alcohol bath freezing method, FIGS. 13-14 were obtained using the −80° C. freezing method, while FIGS. 15-16 were obtained using the controlled rate freezing method. Plates were thawed using a 37° C. water bath as described previously in Example 2. Once thawed, plates were removed from the freezer-safe plastic bag. The ice nucleating device was removed from the wells along with the cryopreservation solution, and fresh cell culture media was added. The plates were then evaluated as in previous experiments. Data shown are representative of multiple experiments. The plates were evaluated using a plate reader as described in Example 2.

FIG. 11 is an image obtained from the Magellan™ software used in combination with the fluorescent microplate reader as described in Example 2. The image portrays the relative fluorescent intensity based on NHDF cell density and metabolic activity for each well as a color for all wells of the test plate. Color associated with fluorescent intensity can also be correlated to viability as depicted on FIG. 12.

As shown in FIG. 11, the addition of the ice nucleating device using the alcohol bath freezing method effectively reduces well to well variability compared to wells not having an ice nucleating device. The wells having the ice nucleating device have a high number of wells with a very similar color range, while the wells without an ice nucleating device have a much wider range of color from one well to another. This is consistent for each of the device designs tested. The large variation in color seen in wells without an ice nucleating device is directly correlated to the increased variability in cell density and viability from well to well. Little or no recovery is noted in any of the wells having media and DMSO with any of the device designs tested. When the relative fluorescent intensity for each of the wells is plotted on a graph as shown in FIG. 12, the large decrease in well to well variability using an ice nucleating device is easily observed from the lower standard deviation for each of the spike designs tested. In FIG. 12, the average relative fluorescent units for the respective well conditions is shown. To demonstrate the range in well to well variability, the standard deviation for wells having an ice nucleating device and those without an ice nucleating device is depicted. The standard deviation is significantly less for the sample wells containing the ice nucleating devices as compared to the standard deviation of the sample wells without an ice nucleating device. In addition, the relative fluorescent units obtained from non-frozen control samples is averaged and shown in FIG. 12. It is important to notice that the standard deviation of the wells with the ice nucleation device is comparable to that of the non-frozen control. The results of this example are consistent with the results described in Example 3. The addition of an ice nucleating device can significantly reduce the well to well variability compared to the cell recovery in wells without an ice nucleating device.

Figure 13:
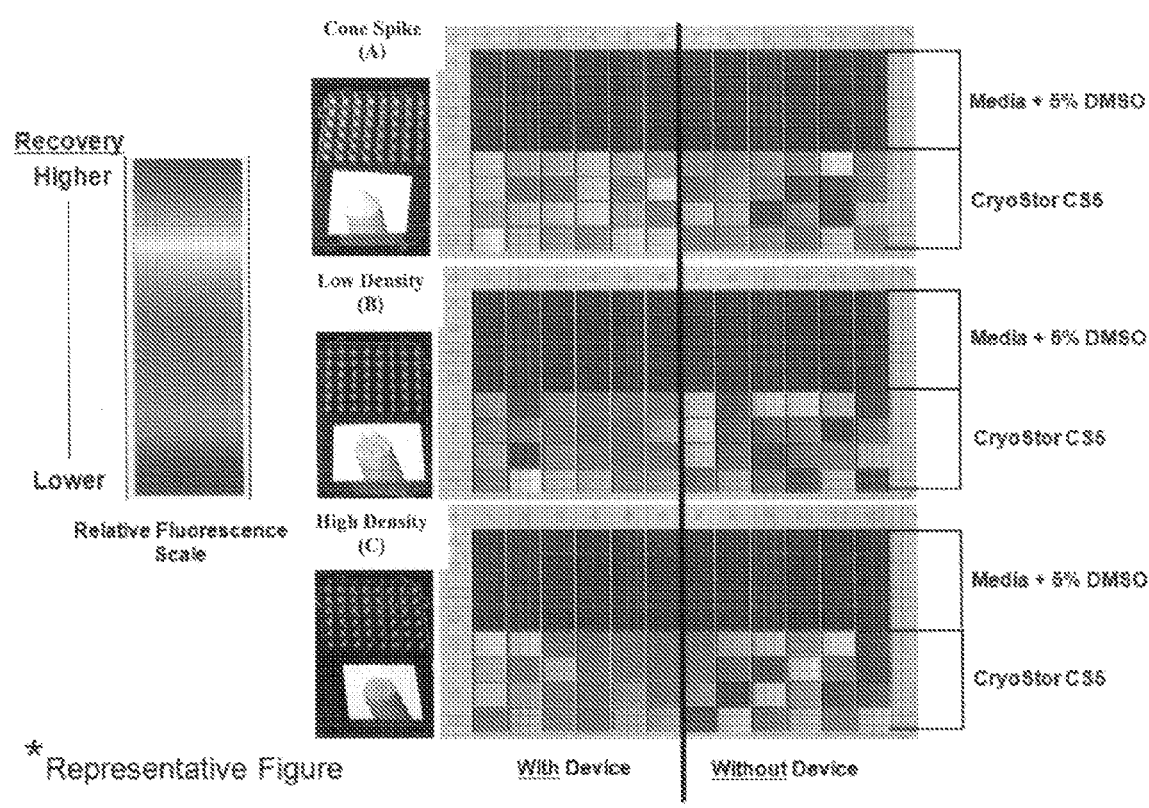
FIG. 13 is a diagram showing the relative fluorescence of Normal Human Dermal Fibroblast (NHDF) cells in each well of a 96-well tissue culture plate following freezing using the −20° C. to directly in a −80° C. freezing method using CRYOSTOR™ CS5 or culture media with serum and 5% DMSO with and without a nucleating device, in accordance with an illustrative embodiment of the invention.

FIG. 13 is an image obtained from the Magellan™ software used in combination with the fluorescent microplate reader as described in Example 2. The image portrays the relative fluorescent intensity based on NHDF cell density and metabolic activity for each well as a color for all wells of the test plate. Color associated with fluorescent intensity can also be correlated to viability as depicted on FIG. 14.

Figure 14:
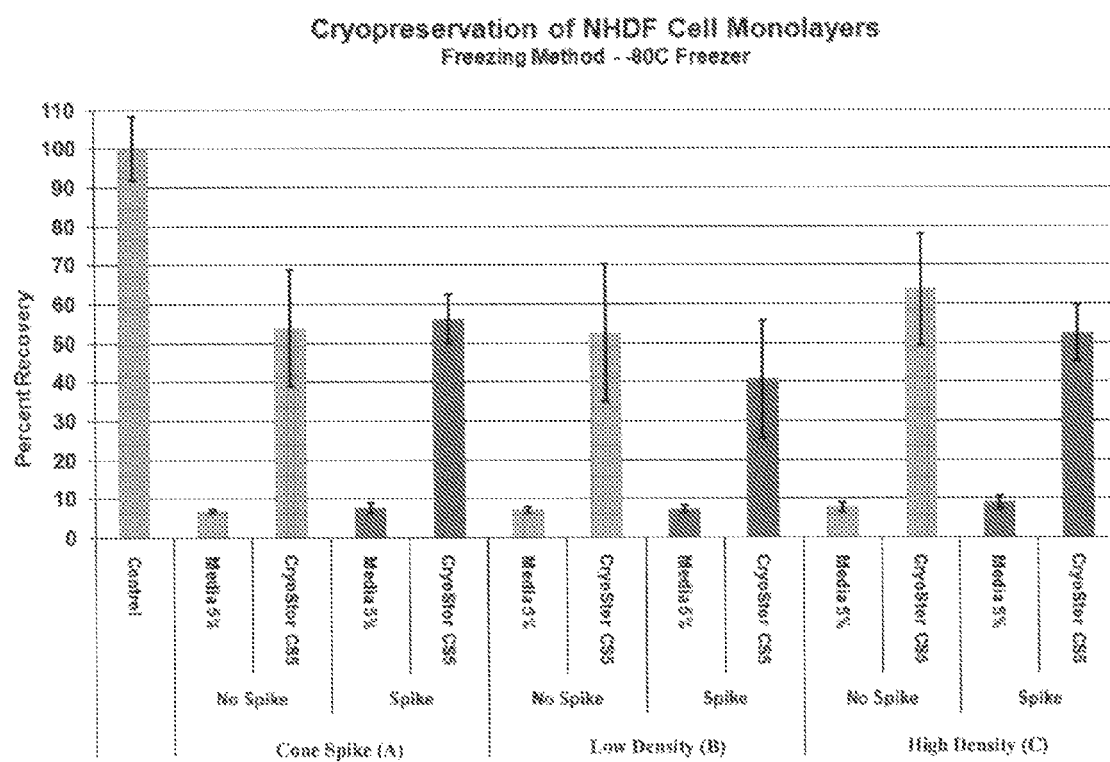
FIG. 14 is a graph showing relative percent viability of NHDF cells following freezing in each of the conditions tested in FIG. 13.

As shown in FIG. 13, the addition of the ice nucleating device using the −80° C. freezing method effectively reduces well to well variability compared to wells not having an ice nucleating device. The wells having the ice nucleating device have a high number of wells with a very similar color range, while the wells without an ice nucleating device have a much wider range of color from one well to another. This is consistent for each of the device designs tested, although it should be noted that the low density array spike device looks to be less effective compared to the other two device designs (single cone spike, high density array). The large variation in color seen in wells without an ice nucleating device is directly correlated to the increased variability in cell density and viability from well to well. Little or no recovery is noted in any of the wells having media and DMSO with any of the device designs tested. When the relative fluorescent intensity for each of the wells is plotted on a graph as shown in FIG. 14, the large decrease in well to well variability using an ice nucleating device is easily observed from the lower standard deviation for each of the spike designs tested. In FIG. 14, the average relative fluorescent units for the respective well conditions is shown. To demonstrate the range in well to well variability, the standard deviation for wells having an ice nucleating device and those without an ice nucleating device is depicted. The standard deviation is significantly less for the sample wells containing the ice nucleating devices as compared to the standard deviation of the sample wells without an ice nucleating device. In addition, the relative fluorescent units obtained from non-frozen control samples is averaged and shown in FIG. 14. It is important to notice that the standard deviation of the wells with the ice nucleation device is comparable to that of the non-frozen control. The results of this example are consistent with the results described in Example 3. The addition of an ice nucleating device can significantly reduce the well to well variability compared to the cell recovery in wells without an ice nucleating device.

Figure 15:
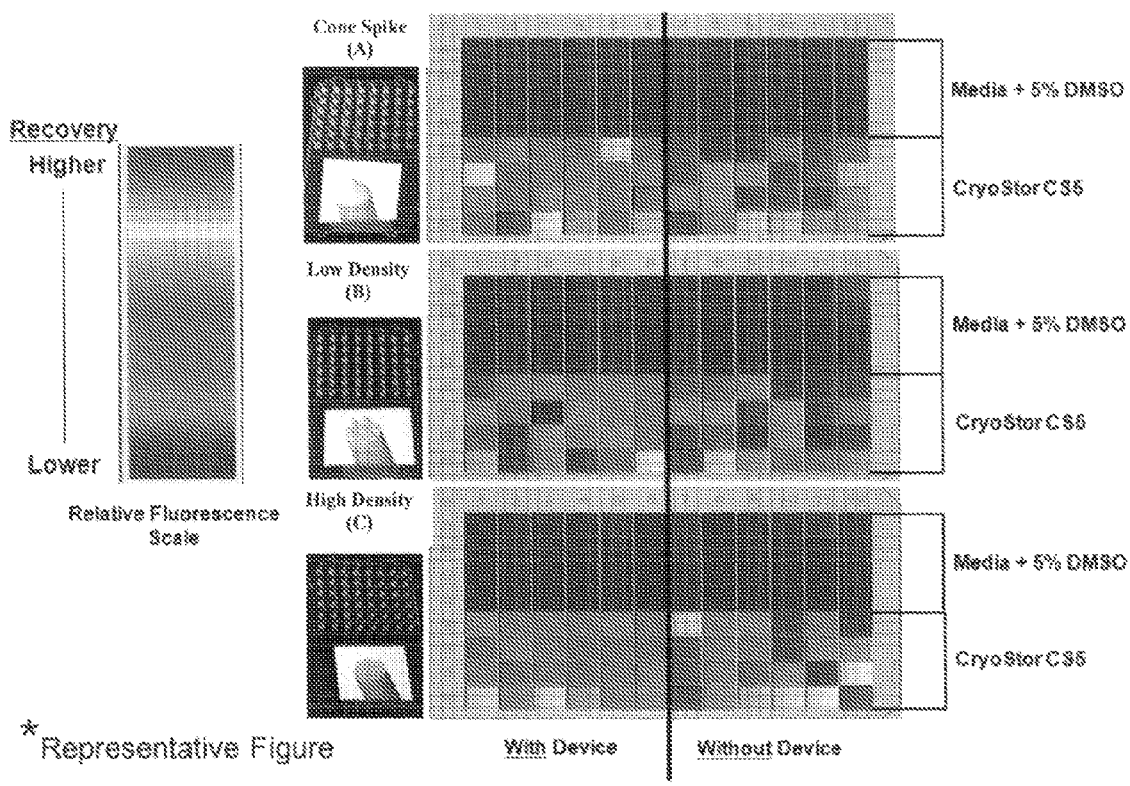
FIG. 15 is a diagram showing the relative fluorescence of Normal Human Dermal Fibroblast (NHDF) cells in each well of a 96-well tissue culture plate following freezing using the controlled rate freezer (−1° C./minute) freezing method using CRYOSTOR™ CS5 or culture media with serum and 5% DMSO with and without a nucleating device, in accordance with an illustrative embodiment of the invention.

FIG. 15 is an image obtained from the Magellan™ software used in combination with the fluorescent microplate reader as described in Example 2. The image portrays the relative fluorescent intensity based on NHDF cell density and metabolic activity for each well as a color for all wells of the test plate. Color associated with fluorescent intensity can also be correlated to viability as depicted on FIG. 16.

Figure 16:
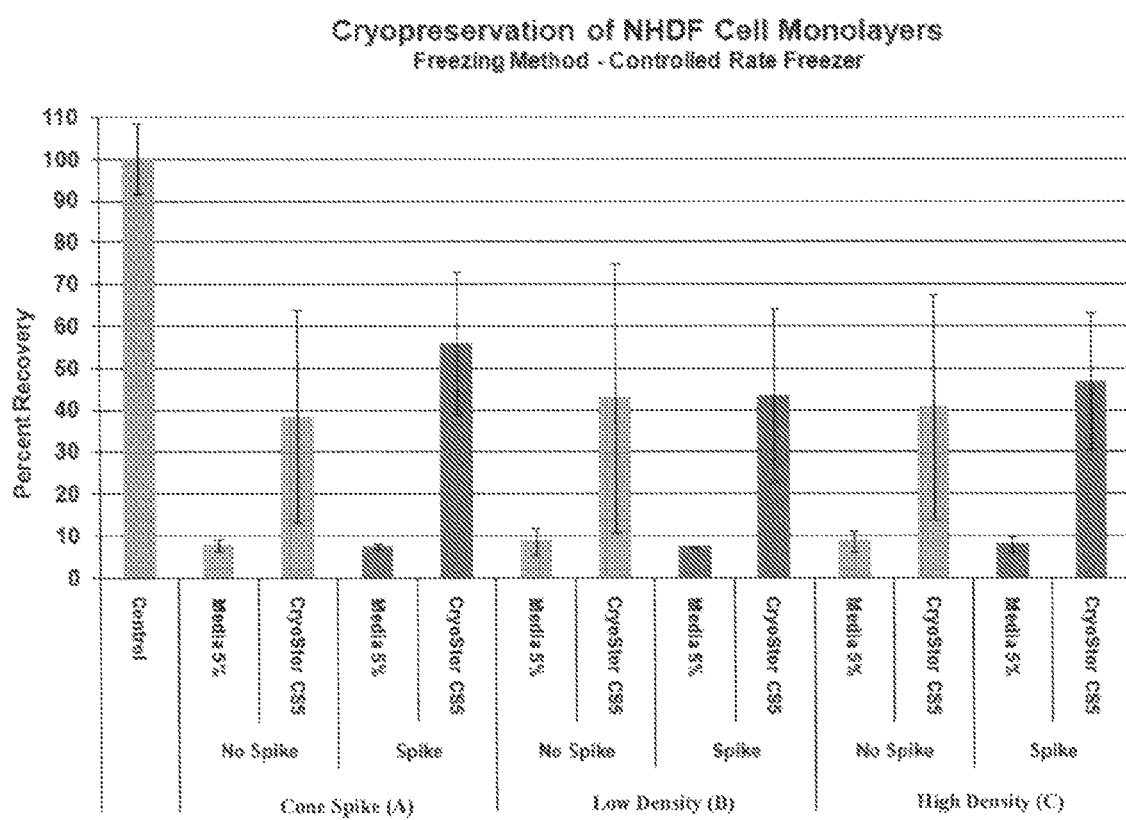
FIG. 16 is a graph showing relative percent viability of NHDF cells following freezing in each of the conditions tested in FIG. 15.

As shown in FIG. 15, the addition of the ice nucleating device using the controlled rate freezing method effectively reduces well to well variability compared to wells not having an ice nucleating device. The wells having the ice nucleating device have a high number of wells with a very similar color range, while the wells without an ice nucleating device have a much wider range of color from one well to another. This is consistent for each of the device designs tested. The large variation in color seen in wells without an ice nucleating device is directly correlated to the increased variability in cell density and viability from well to well. Little or no recovery is noted in any of the wells having media and DMSO with any of the device designs tested. When the relative fluorescent intensity for each of the wells is plotted on a graph as shown in FIG. 16, the large decrease in well to well variability using an ice nucleating device is easily observed from the lower standard deviation for each of the spike designs tested. In FIG. 16, the average relative fluorescent units for the respective well conditions is shown. To demonstrate the range in well to well variability, the standard deviation for wells having an ice nucleating device and those without an ice nucleating device is depicted. The standard deviation is significantly less for the sample wells containing the ice nucleating devices as compared to the standard deviation of the sample wells without an ice nucleating device. In addition, the relative fluorescent units obtained from non-frozen control samples is averaged and shown in FIG. 16. It is important to notice that the standard deviation of the wells with the ice nucleation device is comparable to that of the non-frozen control. The results of this example are consistent with the results described in Example 3. The addition of an ice nucleating device can significantly reduce the well to well variability compared to the cell recovery in wells without an ice nucleating device.

EXAMPLE 6

Freezing of NHDF Cell Monolayers in 96-Well Plate Testing Efficacy and Variability of CRYOSTOR™ CS5 Cryopreservation Media Combined with or without an Ice Nucleating Device and with or without an Insulating Device An insulating device as described in FIG. 2A was inserted around the outer edge of a 96-well plate to and utilized to determine device utility and efficacy compared to having no insulating device. For the provided examples demonstrated in FIGS. 17-18, the ice nucleating device is essentially as described in FIG. 10. The insulating devices were prepared by applying a standard insulating caulk (acrylic latex caulk plus silicone) to the bottom outside edge of a 96-well plate. The insulating device was level with the bottom portion of the plate consistent with the bottom of each of the wells. The device was added to half of each plate, while the right half served as an internal experimental control. The insulating device and plate were maintained overnight at ambient temperature prior to use.

For this study, NHDF cell monolayers were utilized, and cell monolayers were prepared and formed as described in previous examples. NHDF cell monolayers were prepared for cryopreservation essentially as described in Example 2. Briefly, CRYOSTOR CS5 was added to all wells of the plate. Following the addition of the chilled cryopreservation solution, the manufactured ice nucleating device inserts, described in FIG. 10, were placed on the plates. The left half of the ice nucleating insert contained an ice nucleating devices while the right half did not, which allowed for intra-experimental comparison. Once the insert was placed onto the plate, the plate lid was placed on the top. The plates were then sealed and stored for 10 minutes at 2-8° C. as described in Example 3.

Figure 17:
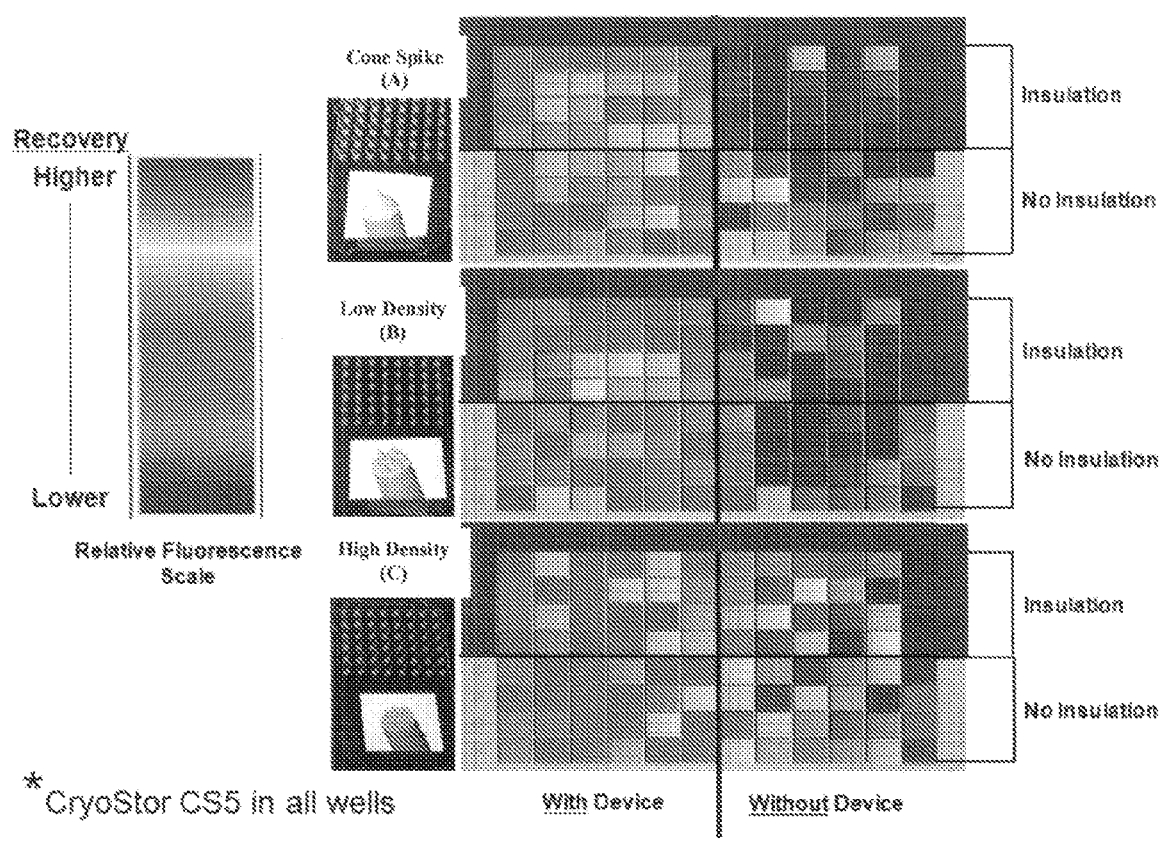
FIG. 17 is a diagram showing the relative fluorescence of Normal Human Dermal Fibroblast (NHDF) cells in each well of a 96-well tissue culture plate following freezing using the −20° C. to directly in a −80° C. freezing method using CRYOSTOR™ CS5 with and without a nucleating device (single cone, low-density array, and high-density array spike devices—FIGS. 10A-C—were used), and with and without an insulating device in accordance with an illustrative embodiment of the invention.

Plates were then frozen using the freezing methods described in Example 2. FIG. 17 was obtained using the −80° C. freezing method, while FIG. 18 were obtained using the controlled rate freezing method. Plates were thawed using a 37° C. water bath as described previously in Example 2. Once thawed, plates were removed from the freezer-safe plastic bag. The ice nucleating device was removed from the wells along with the cryopreservation solution, and fresh cell culture media was added. The plates were then evaluated as in previous experiments. Data shown are representative of multiple experiments. The plates were evaluated using a plate reader as described in Example 2.

FIG. 17 is an image obtained from the Magellan™ software used in combination with the fluorescent microplate reader as described in Example 2. The image portrays the relative fluorescent intensity based on NHDF cell density and metabolic activity for each well as a color for all wells of the test plate.

Figure 18:
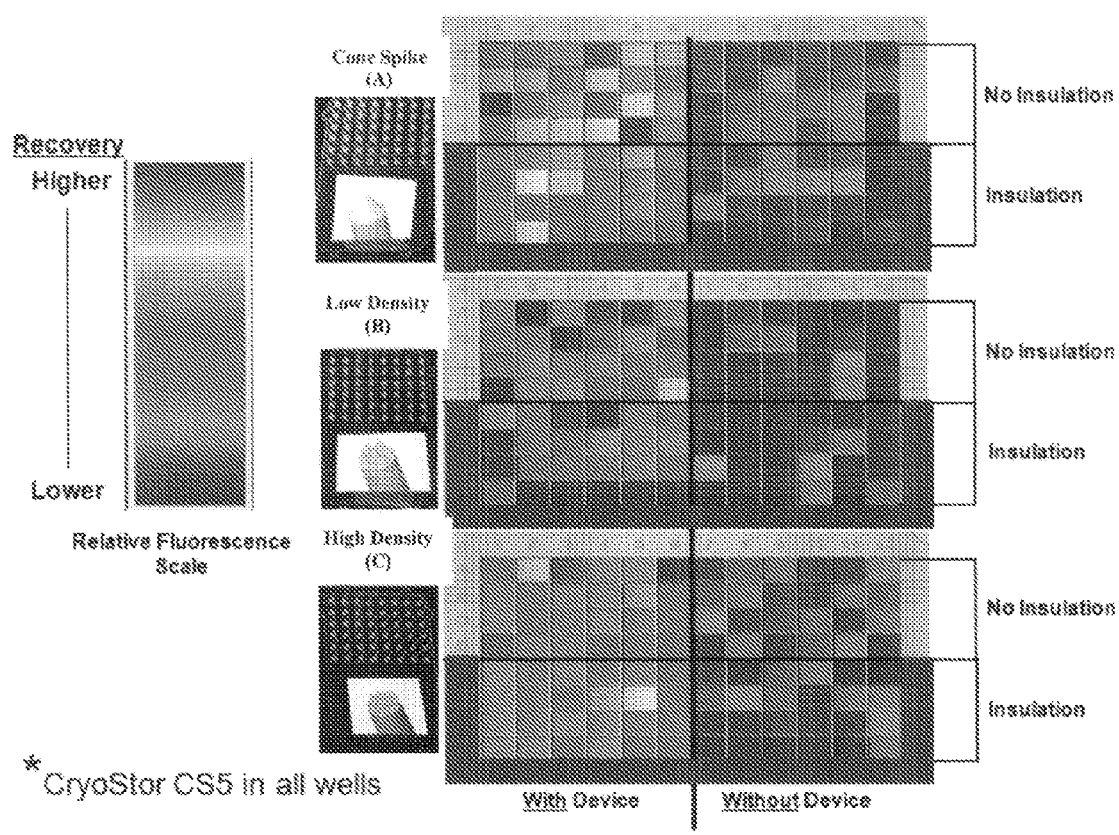
FIG. 18 is a diagram showing the relative fluorescence of Normal Human Dermal Fibroblast (NHDF) cells in each well of a 96-well tissue culture plate following freezing using the controlled rate freezer (−1° C./minute) freezing method using CRYOSTOR™ CS5 or culture media with serum and 5% DMSO with and without a nucleating device (single cone, low-density array, and high-density array spike devices—

As shown in FIGS. 17 and 18, the addition of the insulating device around the outer plate wells of the 96-well plate reduces well to well variability compared to wells not having an insulating device. The improvement is noticeable only in the wells having the ice nucleating device present as well. The outer wells having the insulating device and ice nucleating device have a greater number of wells with a very similar color range compared to the wells only having the ice nucleating device. The slightly higher variation in color seen in wells without an insulating device is directly correlated to the increased variability in cell density and viability from well to well. The addition of an insulating device can aid to reduce the well to well variability compared to the cell recovery in wells without an insulating device.

EXAMPLE 7

Freezing of Human Hepatocyte Cell Monolayers in 96-Well Plate in CRYOSTOR™ CS10 Cryopreservation Media with and without an Ice Nucleating Device Human hepatocyte cell monolayers are frozen with and without a single cone ice nucleating device, low density array, or high density array as described in FIGS. 10A-C to assess device utility and efficacy. Human hepatocyte cell monolayers are prepared and formed as per the manufacturer's instructions in each well of a 96 well plate, and the cell monolayers are prepared for cryopreservation essentially as described in Example 2. Briefly, CRYOSTOR™ CS10 is added to all wells of the plate. Following addition of the chilled cryopreservation solution, an ice nucleating device insert, described above, is placed on the plates. One half of the ice nucleating device insert contains ice nucleating devices while the other half has no devices. This allows for intra-experimental comparison. The ice nucleating device insert is placed on the plate and the plate lid is placed on the top. The plates are then sealed and stored for 10 minutes at 2-8° C. as described in Example 3.

Plates then are frozen using the −80° C. freezing methods and controlled rate freezing methods described in Example 2. Subsequently, plates are thawed using a 37° C. water bath as described previously in Example 2. Once thawed, plates are removed from the freezer-safe plastic bag. The ice nucleating device is removed from the wells along with the cryopreservation solution, and fresh hepatocyte cell culture media is added. The plates are then evaluated for hepatocyte recovery and viability for initial feasibility and overall well to well variability.

In addition, hepatocyte cell function is evaluated to assess and compare the efficacy of nucleating device as compared to wells where no nucleating device is used. The optimal freezing method determined from the initial hepatocyte study above will be used. Plates are prepared and frozen as described previously. Three plates from at least 3 different lots of hepatocytes are tested. Once thawed, cell viability and cell function are evaluated. Hepatocyte function is assessed by albumin secretion, cytochrome P450 analysis, and/or urea synthesis (2 of the 3 assays will be used). Overall function and viability is compared to non-frozen control cultures. Overall well to well variability is assessed as a final measure of the device efficacy.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. Further, the use of "or" means "and/or" unless stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The invention can be embodied in other specific forms without departing from the spirit or essential characteristics thereof. The present embodiments are therefore to be considered illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for cryopreserving a plurality of cell monolayers for high throughput screening, the apparatus comprising:
    a multiwell tissue culture vessel comprising a biocompatible substrate, wherein each well of the multiwell vessel comprises an interior and an exterior; and,
    a plurality of mechanical ice nucleating devices arranged so that at least one mechanical ice nucleating device is disposed in the interior of each of a plurality of wells of the multiwell vessel, the mechanical ice nucleating device comprising a three-dimensional protrusion attached to a separable cover or a separable insert for the multiwell vessel such that the protrusion occupies the interior space of the well when the cover or the insert is placed on the multiwell vessel.

2. The apparatus of claim 1, wherein the protrusion is plastic.

3. The apparatus of claim 1, wherein the protrusion is attached to the vessel cover.

4. The apparatus of claim 1, wherein the protrusion is attached to the vessel insert.

5. The apparatus of claim 3, wherein the at least one protrusion is integral with the cover.

6. The apparatus of claim 4 wherein the at least one protrusion is integral with the insert.

7. The apparatus of claim 3, wherein the protrusion is hollow, solid, or semi-permeable and needle-like, sphere-like, pyramid-like, or cone-like in shape.

8. The apparatus of claim 4, wherein the protrusion is hollow, solid, or semi-permeable and needle-like, sphere-like, pyramid-like, or cone-like in shape.

9. The apparatus of claim 1, further comprising a cryopreservation medium disposed in the plurality of wells.

10. The apparatus of claim 1, comprising:
    an insulating material occupying free space surrounding a plurality of the wells of the multiwell vessel to aid in consistent cooling and warming of all wells;
    wherein the apparatus is sterile, and
    wherein the protrusion and insulation reduce well-to-well variability of the cell monolayers post-thaw.

11. The apparatus of claim 10, wherein the insulating material is comprised of the same material as the vessel.

12. The apparatus of claim 10, wherein insulating material occupies any or all of the wells, so as to fill the air space above the top level of the cells and cryoprotectant media and the lower or bottom surface of the lid or cover.

13. The apparatus of claim 1 comprising:
    a cell monolayer disposed in the interior of each of the plurality of wells; and
    a biopreservation medium disposed in the interior of each of the plurality of wells, the biopreservation medium in contact with the cell monolayers.

14. The apparatus of claim 13, wherein the cells comprise primary cells, immortalized cells, or tissue.

15. The apparatus of claim 1, wherein the protrusion comprises at least one secondary protrusion to provide additional ice nucleation sites.

16. The apparatus of claim 1, wherein the three-dimensional protrusion is pointed.

17. The apparatus of claim 13, further wherein the three-dimensional protrusion is configured to contact the biopreservation medium.

* * * * *